United States Patent [19]

Curtiss et al.

[11] Patent Number: 4,778,752

[45] Date of Patent: Oct. 18, 1988

[54] RECEPTORS SPECIFIC FOR HAPTEN-MODIFIED SELF PROTEINS

[75] Inventors: Linda K. Curtiss; Joseph L. Witztum, both of San Diego, Calif.

[73] Assignee: Scripps Clinic and Research Foundation, La Jolla, Calif.

[21] Appl. No.: 941,517

[22] Filed: Dec. 17, 1986

Related U.S. Application Data

[63] Continuation of Ser. No. 540,839, Oct. 11, 1983, abandoned.

[51] Int. Cl.[4] .................. G01N 33/53; G01N 33/577; C12N 15/00
[52] U.S. Cl. .......................................... 435/7; 435/68; 435/172.2; 435/240.27; 435/810; 435/948; 436/67; 436/87; 436/548; 436/808; 530/387; 530/388; 935/89; 935/93; 935/95; 935/96; 935/99; 935/100; 935/106; 935/110
[58] Field of Search ............ 435/7, 68, 122.2, 240.27, 435/810, 948; 436/67, 87, 548, 808; 530/387, 388; 935/89, 93, 95, 96, 99, 100, 106, 110

[56] References Cited

U.S. PATENT DOCUMENTS

| | | | |
|---|---|---|---|
| 3,839,153 | 10/1974 | Schuurs et al. | 195/103.5 R |
| 3,879,262 | 4/1975 | Schuurs et al. | 195/63 |
| 4,196,265 | 4/1980 | Koprowski et al. | 435/2 |
| 4,247,533 | 1/1981 | Cerami et al. | 424/1 |
| 4,416,866 | 11/1983 | Strand | 436/1.1 |
| 4,434,156 | 2/1984 | Trowbridge | 424/85 |
| 4,452,903 | 6/1984 | Lee et al. | 436/540 |
| 4,478,744 | 10/1984 | Mezei et al. | 424/88 |

OTHER PUBLICATIONS

J. Biological Chemistry. 257, 15213 (1982) Curtiss et al., Immuno Chemical Heterogeneity of Human Plasma Apolipoprotein B: I. Apolipoprotein B Binding of Mouse Antibodies.

J. Biological Chemistry. 257, 15222 (1982) Tsao et al., Immunochemical Heterogeneity of Human Plasma Apolipoprotein B: II. Expression of Apolipoprotein B Epitopes on Native lipoproteins.

Obermayer et al., Wien. Klin. Wochenschr., 19:327–334 (1906).

Good Friend et al., Science, 144:1344 (1968).

Primary Examiner—Christine M. Nucker
Attorney, Agent, or Firm—Dressler, Goldsmith, Shore, Sutker & Milnamow

[57] ABSTRACT

Epitope-specific reagents in the form of receptors that bind to hapten-modified proteins and do not bind to unmodified proteins, methods of their preparation and use, along with diagnostic systems for measuring the presence and amount of hapten-modified protein in an assayed sample are disclosed. In particular, monoclonal antibodies that bind reduced glycosylated proteins (for example, reductively glucosylated proteins including human plasma lipoproteins), but do not react with non-reduced glycosylated proteins, reduced non-glycosylated proteins or non-reduced non-glycosylated proteins are produced and utilized.

90 Claims, 7 Drawing Sheets

IDENTIFICATION OF GLUCITOLLYSINE RESIDUES IN PLASMA

RECEPTORS SPECIFIC FOR HAPTEN-MODIFIED SELF PROTEINS

This application is a continuation, of application Ser. No. 540,839, filed Oct. 11, 1983 abandoned.

DESCRIPTION

1. Technical Field

The present invention contemplates epitope-specific reagents that bind to hapten-modified proteins and do not bind to unmodified proteins, methods of their preparation and use, along with diagnostic systems for measuring the presence and amount of hapten-modified protein in an assayed sample. More particularly, the present invention contemplates monoclonal antibodies that bind reduced glycosylated proteins (for example, reductively glucosylated proteins including human plasma lipoproteins), but do not react with non-reduced glycosylated proteins, reduced non-glycosylated proteins or native non-reduced non-glycosylated proteins.

2. Background Art

The circulatory system is aqueous based and thus only transports water soluble substances. Compounds such as cholesterol, triglycerides and other like substances, however, are not soluble in water. In order for these substances, which are generally referred to as lipids, to be transported in the blood plasma of the circulatory system they are dispersed in water soluble units called lipoproteins.

A lipoprotein is a combination of a lipid and a protein that has the general properties (e.g., solubility) of proteins. A lipid is any of a heterogenous group of fats and fatlike substances characterized by being water-insoluble and being extractable by organic solvents such as alcohol, ether, chloroform, benzene, etc. All lipids contain aliphatic hydrocarbons as a major constituent. Practically all of the lipids of plasma are present as lipoprotein complexes of which the principal types, alpha-, prebeta- and beta-lipoproteins, can be readily distinguished by electrophoresis. The beta-lipoproteins transport more of the total plasma cholesterol, contain a higher concentration of both free and esterified cholesterol and have a higher cholesterol/phospholipid ratio than alpha-lipoproteins.

Each lipoprotein particle contains a nonpolar core, in which many molecules of hydrophobic lipid are packed to form an oil-like droplet. This hydrophobic core, which accounts for most of the mass of the particle, consists of triglycerides and cholesteryl esters in varying proportions. Surrounding the core is a polar surface coat of phospholipids that stabilize the lipoprotein particle so that it can remain in solution or dispersed in the plasma. In addition to phospholipids, the polar coat contains small amounts of unesterified cholesterol. Each lipoprotein particle also contains specific proteins (called apoproteins) that are partly exposed at the surface. The apoprotein binds to specific enzymes or transport proteins on cell membranes, thus directing the lipoprotein to its sites of metabolism.

There are four principal types of lipoproteins which can be identified according to their density. The four types of lipoproteins are chylomicrons (having the lowest density of the four types), very low density lipoproteins, low density lipoproteins and high density lipoproteins. These four types of lipoproteins primarily differ in their composition of lipid and protein. As indicated above, the lipids and proteins are not covalently joined but are held together largely by hydrophobic interactions between the nonpolar portions of the lipid and protein components.

A chylomicron is a stable globular structure containing approximately 86 percent triglycerides, 3 percent cholesterol, 9 percent phospholipids and 2 percent protein that is found in the intestinal lymphatics (lacteals) and the blood during and after meals. This is the form in which absorbed long-chain fats and cholesterol are transported from the intestine. A very low density lipoprotein (VLDL) is a plasma lipoprotein complex containing relatively little protein by weight, high levels of triglycerides, and moderate concentrations of both phospholipids and cholesterol. A low density lipoprotein (LDL) is a plasma lipoprotein complex containing moderate levels of protein by weight, low levels of triglycerides, moderate levels of phospholipids and high levels of cholesterol. A high density lipoprotein (HDL) is a plasma lipoprotein complex containing high levels or concentrations of protein, low levels of triglycerides, moderate levels of phospholipids and relatively little cholesterol.

As discussed before, lipoproteins circulate in the blood stream. Also, circulating in the blood stream are glucose molecules. To a certain extent, a non-enzymatic, protein-modifying reaction occurs in the circulatory system whereby glucose is added to the protein component of the lipoprotein. This reaction is referred to as "glucosylation." The term "non-enzymatic", as used herein, means that a reaction occurs on its own without being mediated by other proteins.

The non-enzymatic addition of glucose is not limited only to lipoproteins. Glucose adds in a similar manner to other proteins including hemoglobin. Hemoglobin is found in blood and its principal function is to transport oxygen. Sugars other than glucose also can add to a protein in a non-enzymatic manner. The addition of any sugar to a macromolecule is called glycosylation, while as previously indicated, the addition of glucose is called glucosylation.

Glycosylation ordinarily occurs at an N-terminus of a macromolecule and, with particular reference to proteins, at the epsilon amine of a lysine residue of the protein. Specifically, a protein can be viewed as being comprised of amino acid building blocks which are linked together in a chain. There are twenty-two commonly occurring amino acids from which proteins and other biological substances are formed.

When glucose adds to the protein, it can react with a lysine (or with the free amino group of an N-terminus amino acid) to form a labile intermediate called a Schiff base. The Schiff base can undergo further transition to form either of two chemical species—(1) glucitollysine or (2) a hemiketal/ketoamine, also known as an Amadori rearrangement product. An Amadori rearrangement involves the conversion of an N-glycoside of an aldose sugar into an amino derivative of the corresponding ketose. Hodge in *Advances of Carbohydrate Chemistry*, vol. 10, 169 (1955). Glucitollysine is the alcohol aldose species that is formed by reduction of the Schiff base.

In a diabetic individual, the non-enzymatic glucosylation of plasma proteins is enhanced such that the concentration of glucosylated protein in the blood plasma of a diabetic is two to ten fold higher than the concentration of the same protein in a non-diabetic individual. The glucosylation of proteins is implicated in several pathological complications of diabetes. First, the addition of glucose to lipoproteins is believed to play a role in premature atherosclerosis of diabetics. [Witztum et al., *Diabetes*, 31, 382 (1982) and Witztum et al., *Diabetes*, 31, 1029 (1982).] Second, the glucosylation of lens crystallin of the eye results in opacification and may contribute to cataract formation [Stevens et al., *Proc. Natl. Acad. Sci. USA*, 75, 2918 (1978)]. Third, glucosylation of collagen, a fiber-like protein giving structural support to many tissues, leads to the stiffening of tissue [Kohn et al., *Diabetes*, 31, (Suppl. 3), 47 (1982)]. Finally, glucosylation of proteins has been implicated in functional disturbances of the peripheral nervous system.

In addition, the glucosylation of hemoglobin and other plasma proteins is of considerable clinical interest. For example, the extent of glucosylation provides a useful marker for monitoring blood glucose concentrations in diabetics over a given time period [Bunn, *Diabetes*, 30, 613 (1981) and Goldstein et al., *Diabetes*, 31 (Suppl. 3), 70 (1982)].

The commonly used ion exchange method for measuring the concentration of glucosylated hemoglobin ($HbA_{1C}$) is discussed in Garlick et al., *J. Clin. Invest.*, 71, 1062 (1983). That method, however, suffers from several complications and is of limited utility. In addition, hemoglobin has a long half-life in the blood stream, and as a result, measurements are relatively insensitive to frequent changes in glucose concentration.

It is desirable to have an assay that measures the extent of glucosylation of a specific plasma protein with a shorter half-life than hemoglobin. Thus, ambient blood glucose levels of diabetic individuals could be assessed over relatively short periods of time.

Javid et al., *British J. Hemat.*, 38, 329 (1978) attempted to measure $HbA_{1C}$ by an immunological method. However, their assay utilizes antibodies acquired by conventional procedures which react with non-glucosylated hemoglobin. Such non-specific antibodies must be removed prior to use of the antibody preparation, leaving antibodies that bind to the desired $HbA_{1C}$ molecules but are of low affinity. The required purification and low avidity of the remaining antibodies complicate measurements. An assay that employs antibodies that are specific for the glucose adduct and that exhibit a high affinity is needed.

As previously stated, glucosylated low density lipoproteins are implicated in atherosclerosis. Thus, it would be of significant clinical value to be able to readily quantitate the level of glucosylated low density lipoproteins in the plasma of diabetic individuals. Even more so, it would be beneficial to be able to quantitate the level of any glycosylated macromolecule.

The conventional procedure for generating such antibodies which recognize, for example, only human glucosylated low density lipoprotein and not native lipoprotein is to immunize an animal (for example, a mouse) with human glucosylated low density lipoprotein. The immune system of the mouse recognizes certain regions, called determinants, of the glucosylated, human low density lipoprotein as being foreign and produces an antibody response against those determinants. An epitope is a particular chemical structure present within a determinant on an antigenic molecule that determines immunogenic and antigenic specificity.

Human glucosylated low density lipoproteins, like most immunogens, contain many epitopes and one or more different antibodies is usually raised against each determinant. Thousands of immune cells in the mouse secrete antibodies which are specific for the various epitopes of a glucosylated low density lipoprotein. The majority of these antibodies would be directed against portions of the native protein [Curtiss et al., *J. Biol Chem.*, 257, 15213 (1983)] and only a very small fraction of these cells secrete the desired antibody against the glucosylated, epitopic region of the protein.

Antibodies are secreted by specialized cells called B cells (bone marrow-derived lymphocytes). Each B cell secretes one type of antibody having a single specificity. So the various antibodies of different specificites are each secreted by different B cells.

To harvest the antibodies, the B cells are cloned. This is accomplished by removing the B cells from the animal, fusing the B cells with a cancerous or myeloma cell to form a cell hybrid (called "a hybridoma") and then culturing the hybridoma.

The fusion of mouse myeloma cells to spleen cells from immunized mice by Kohler and Milstein in 1975 [*Nature*, 256, 495 (1975)] demonstrated for the first time that it was possible to fuse antibody-producing cells with tumor cells to obtain a continuous cell line making homogenous (so-called "monoclonal") antibody. Since that time, much effort has been directed to the production of various hybridomas and to the use of the antibody made by these hybridomas for various scientific investigations. See, for example, *Current Topics in Microbiology and Immunology*, Volume 81—"Lymphocyte Hybridoma", Melchers et al., Eds., Springer-Verlag (1978), and the references contained therein; Barnstable et al., *Cell*, 14, 9 (1978); Parham et al., *Nature*, 276, 397 (1978); and *Handbook of Experimental Immunology*, Third Edition, Volume 2, Ch. 25, Wier, Ed., Blackwell (1978).

Moreover, a technique called "electrofusion" recently developed by the Nuclear Research Center, Kernforschungsanlage (KFA) of West Germany is reported to be more efficient at forming hybridomas than the methods of Kohler and Milstein (*Biotechnology*, 1, 390, July 1983). That technique uses electric fields to fuse cells including antibody-producing cells with tumor cells to yield continuous monoclonal antibody producing cell lines.

Those publications indicate the rewards and complications of attempting to produce monoclonal antibodies from hybridomas. While the general techniques of cell fusion are well understood conceptually, there are many difficulties met and variations required for each specific case. In fact, there is no assurance, prior to attempting to prepare a given hybridoma, that the desired hybridoma will be obtained, that it will produce antibody if obtained, or that the antibody so produced will have the desired specificity. The degree of success is influenced principally by the type of immunogen employed and the selection technique used for isolating the desired hybridoma.

To prepare monoclonal antibodies against modified proteins using conventional techniques, desired clones are selected by a double screening, or differential screening, technique. Double screening is a process whereby the antibodies are first tested (screened) for reactivity with the modified protein and are then screened for non-reactivity with the unmodified protein. Using such conventional methods, thousands of hybridomas must be made and then double screened to identify the few clones that produce the desired monoclonal antibody.

It would be desirable to have a technique to direct the immune response of the host against the specific moiety to be assayed; e.g., a reduced glycosylated protein epitope. Thus, a high percentage of the hybridomas would produce monoclonal antibodies that are specific for the exemplary reduced glycosylated protein and do not react with the native protein or the non-reduced glycosylated protein. Such a heretofore unavailable technique would avoid the need to make and double screen thousands of hybridomas in order to select the few desired clones.

Moreover, it would be desirable to be able to determine the particular form of the glycosylated lysine. As previously explained, glucosylated lysine residues (one type of glycosylated lysine) can exist in one of three forms: glucitollysine, a Schiff base intermediate or an Amadori rearrangement product.

BRIEF SUMMARY OF THE INVENTION

The present invention contemplates an epitope-specific reagent, a method of its preparation and use, and a diagnostic system utilizing that reagent. The epitope-specific reagent comprises a receptor, raised in an animal host to an immunogenic, hapten-modified protein. The immunogenic protein itself comprises a chemically modified protein, such as a hapten-modified low density lipoprotein, that is a homologous or autologous (self) protein as to the host animal and is non-immunogenic when introduced into the host as the chemically unmodified homologous or autologous protein. The receptor binds to the hapten-modified, immunogenic protein but not to the unmodified protein.

Monoclonal antibodies that bind to reduced glycosylated human plasma lipoproteins but do not bind to native or non-reduced glycosylated human plasma lipoproteins are particularly preferred embodiments of the epitope-specific reagents.

According to the present invention, a method of forming an epitope-specific reagent comprises the steps of:

(a) administering to a host an immunogenic, hapten-modified protein in an amount sufficient to induce the production of antibodies to the epitope of the hapten-modified protein, the protein being non-immunogenic (because it is an autologous or homologous protein) in the host in an unmodified form; and (b) recovering the antibodies so induced.

Monoclonal antibodies are prepared by the steps of:

(a) administering to a host an immunogenic, hapten-modified protein in an amount sufficient to induce the production of antibodies to the epitope of the hapten-modified protein, the protein being non-immunogenic (because it is an autologous or homologous protein) in the host in an unmodified form;

(b) recovering the antibody-producing cells from the host;

(c) forming cell hybridomas by fusing the antibody producing cells with myeloma cells;

(d) culturing the hybridomas so formed; and (e) collecting the monoclonal antibodies as a product of said hybridomas.

The above method also can include the step of administering to the host, after step (a) but before step (b), a second immunogenic protein in a hapten-modified form in an amount sufficient to induce the production of antibodies to the epitope of the modified form, the epitope of the second immunogenic protein being substantially similar to the epitope of the first-named immunogenic protein and the second protein being immunogenic in the host in an unmodified form. The phrase "substantially similar", as used herein, means the second protein is modified in the same manner as the first protein. To specifically propagate in vivo those clones of cells making antibodies against the first hapten-modified immunogenic protein that cross react with the second hapten-modified immunogenic protein, the second hapten-modified immunogenic protein is used as the final intravenous booster before fusion of the cells to form hybridomas. This second immunogenic protein is referred to herein as the prefusion immunogen. Thus, from a single cell fusion, a large number of hybridomas is obtained that secrete antibody capable of binding to the second immunogenic protein in the hapten-modified, but not in the unmodified form.

The particularly preferred monoclonal antibodies are produced by a hybridoma selected from the group consisting of hybridomas ATCC CRL HB 8355, HB 8356, HB 8357, HB 8359, HB 8358 and HB 8354. Moreover, the immunogenic protein is a glycosylated plasma protein selected from the group consisting of a lipoprotein, hemoglobin, albumin and transferrin which in the modified form is a reduced, glycosylated protein. The particularly preferred epitope-specific reagents immunoreact with a reduced glycosylated protein, but do not immunoreact with the native protein or a non-reduced glycosylated protein.

The above-described method of preparing monoclonal antibodies can include culturing the hybridoma in vitro in a suitable medium and recovering the antibody from the hybridoma supernatant. This is known as a cell culture system. The above method, in the alternative, can include injecting the hybridoma into an animal host and recovering the antibody from ascites fluid of the host. Such whole animal systems tend to produce more antibody per unit volume than cell culture systems, but whole animal systems are sometimes difficult to use if large quantities of antibody are desired.

The present invention also includes the monoclonal antibodies produced by any of the above described methods. As will be described in greater detail hereinafter, those antibodies can be defined in terms of their reactivity with substrates. For example, one monoclonal antibody of this invention produced by a hybridoma formed by fusion of a mouse myeloma cell line and a spleen cell from a mouse previously immunized first with a mouse (murine) reduced glucosylated protein and then boosted with a reduced human glucosylated protein, reacts with the reduced human glucosylated protein, glucitollysine, glucitolpolylysine, arginine, mannitol, methionine and lysine, but not a non-reduced glucosylated protein, a reduced non-glucosylated protein, a non-reduced non-glucosylated protein, glucose or mannose.

The invention further includes a diagnostic system such as a kit that includes at least one package containing as an active ingredient an effective amount of the epitope-specific reagent of this invention which when introduced into a sample to be assayed (for example, blood plasma) reacts with a hapten-modified self protein such as a reduced glycosylated protein but does not react with an unmodified self protein such as a non-reduced non-glycosylated protein as a measure of the hapten-modified self protein in the sample.

Moreover, the invention includes a method for assaying for the presence of an antigenic, hapten-modified protein in a sample. That method comprises the steps of:

(a) providing an epitope-specific reagent of this invention;

(b) admixing a predetermined amount of the epitope-specific reagent with a predetermined amount of sample to be assayed for the presence of the antigenic, hapten-modified protein to which the epitope-specific reagent binds;

(c) maintaining that admixture for a period of time sufficient for said epitope-specific reagent to bind to the antigenic, hapten-modified protein present in the admixed sample; and (d) determining the amount of binding between said epitope-specific reagent and said antigenic, hapten-modified protein.

In particularly preferred practice, the above method utilizes one of the before-discussed monoclonal antibodies as the epitope-specific reagent.

The word "antigen" in its various grammatical forms has been used in the art to include materials that are immunogenic. However, more recent usage defines an antigen as that to which a receptor binds, and an immunogen as that which induces the production of antibodies in vivo, respectively.

An especially preferred assay method is used to determine the presence and amount of a modified protein (for example, a reduced glycosylated protein) by means of a tandem assay. This tandem assay comprises the steps of:

(a) providing a first receptor covalently attached in a known amount to a solid support such as agarose beads or microtiter wells, the first receptor binding to a first epitope of a protein to be assayed when the protein is in hapten-modified and unmodified forms;

(b) providing a second receptor that binds to a second epitope of the protein to be assayed when that protein is in hapten-modified or unmodified forms;

(c) providing an epitope-specific reagent of this invention that binds to a third epitope of the protein that is present only when the protein is in hapten-modified form;

(d) admixing a predetermined amount of said covalently attached-first receptor and a predetermined amount of a sample to be assayed for the presence of antigenic, hapten-modified protein to which the epitope-specific reagent binds as well as for the presence of the unmodified protein to which the first and the second receptors bind;

(e) maintaining that admixture for a period of time sufficient for said covalently attached first receptor to bind hapten-modified and unmodified proteins present and form binding complexes therewith;

(f) separating the formed binding complexes from the remainder of the admixture;

(g) dividing the formed binding complexes into at least a first aliquot and a second aliquot;

(h) admixing the first aliquot with a predetermined amount of the second receptor and maintaining that admixture for a period of time sufficient to form second binding complexes between the second receptor and the first-formed binding complexes;

(i) determining the amount of second binding complexes formed to thereby determine the total amount of both hapten-modified and unmodified protein present in the sample;

(j) admixing the second aliquot with a predetermined amount of the epitope-specific reagent of this invention and maintaining that admixture for a period of time sufficient to form a third binding complex between the epitope-specific reagent and hapten-modified protein present in the first-formed binding complexes; and (k) determining the amount of third binding complex formed to thereby determine the amount of hapten-modified protein present in the sample.

In the above assay, the first and second receptors may be monoclonal antibodies that bind to different epitopes of apoprotein B-containing lipoproteins. The epitope-specific reagent of this invention may be a monoclonal antibody such as that designated G8H6, discussed hereinafter, that binds selectively to glucitollysine residues of hapten-modified proteins. The second receptor and epitope-specific reagent may contain labels such as $^{125}I$ to facilitate quantitative determinations.

Although the following description refers to the production of antibodies specific for glucosylated proteins that can be used to identify residues hapten-modified by glucosylation, it will be understood that the invention also related generally to the production of antibodies specific for any self protein that is modified to form an immunogenic protein by glycosylation, acylation, alkylation or the like. For example, polyclonal receptors have been prepared by reductive methylation, reductive ethylation and reductive acetylation of murine low density lipoproteins. Moreover, a polyclonal receptor was prepared by the reductive glucosylation of guinea pig low density lipoprotein to form a glc(RED)-LDL.

Moreover, the method of the invention as described herein relates to the non-enzymatic modification of lysine residues with glucose. The chemical reaction described, however, applies to any sugar provided the compound includes an aldehyde group. The reaction also leads to modification of all free amines including the N-terminus of a protein so that the method is applicable to the production of antibodies specific for a hapten-modified N-terminus of a protein.

The present invention can be used, for example, as an index to assess ambient blood glucose levels of diabetic individuals over relatively short periods of time by measuring the glucosylation of cellular, interstitial, plasma or urine proteins with turn-over rates that are shorter than that of hemoglobin.

The present invention can also be used to quantitate glucosylated low density lipoproteins in diabetic individuals, and generally to quantitate the level of any hapten-modified protein for which there is an antibody specific against that protein. In addition, the present invention can determine the state of the glucosylated adduct by exposing the sample to a selective reducing agent.

In its broad sense, the present invention can be applied to produce receptors that bind to any immunogenic modification of a homologous or autologous protein or lipoprotein. More specifically, this invention can be applied to produce monoclonal antibodies that bind to reduced glycosylated proteins, but do not react with non-reduced non-glycosylated proteins.

Still further advantages and benefits of the present invention will become apparent to those skilled in the art from the detailed description, examples and claims which follow.

BRIEF DESCRIPTION OF THE DRAWINGS

In the drawings, which constitute a portion of this disclosure.

DETAILED DESCRIPTION OF THE INVENTION

I. Introduction

Figure 1:
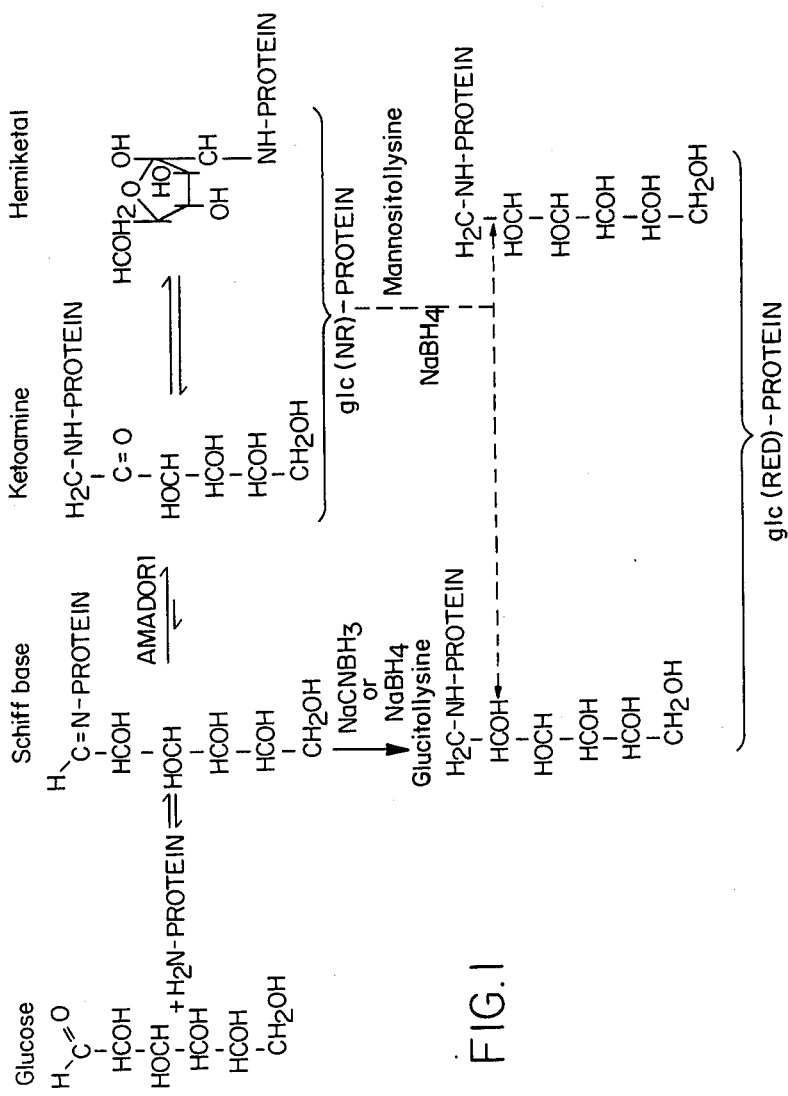
FIG. 1 illustrates the reaction scheme for the non-enzymatic glucosylation of free amines of a protein, e.g. low density lipoproteins (LDL), and the subsequent reduction of intermediate and final products.

Modifications of plasma lipoprotein structure and function resulting from in vivo post-translation non-enzymatic glycosylation may play a role in the premature atherosclerosis of patients with diabetes mellitus. The following description relates to the generation and characterization of six representative murine monoclonal antibodies that bind glucosylated human plasma lipoproteins, but do not react with normal plasma lipoproteins. This was accomplished by immunizing mice with homologous glucosylated low density lipoprotein (LDL). Using competitive inhibition radioimmunoassays, the dominant epitope recognized by these antibodies on glucosylated low density lipoprotein was identified as glucitollysine, which is the reduced hexose alcohol form of glucose conjugated to the epsilon amino group of lysine.

The antibodies were used to identify glucitollysine epitopes on reduced glucosylated isolated proteins including lipoproteins, albumin, hemoglobin and transferrin. These antibodies were also capable of identifying and quantitating glucitollysine residues on the total plasma proteins of diabetic and non-diabetic individuals after reduction of the plasma proteins with sodium borohydride. Data suggest that total diabetic plasma proteins contain about 2- to about 10-fold more glucitollysine residues than non-diabetic plasma proteins.

In addition, a plasma assay for immunochemically quantitating the glucitollysine residues on proteins such as apo B-lipoproteins and albumin is described. This assay does not require prior isolation of the assayed protein and is readily applicable to measuring the extent of glucosylation of any protein of interest.

The method described herein allows the production of region specific antibodies to any immunogenic residue of a protein. Specifically, a reductase that is capable of reducing the Schiff base intermediate of a glycosylation reaction in vivo has not been described. As a result, the Schiff base intermediate forms predominantly the Amadori rearrangement products which are relatively stable in blood plasma. The reduction of a glucosylated protein adduct in vitro quantitatively results in the formation of glucitollysine-containing protein adduct which is chemically distinct from the Amadori rearrangement products. The glucitollysine or other glycosylation adduct will not undergo an Amadori rearrangement, and the formation of the glucosylated adduct starting material from the glucitollysine adduct is unfavorable from both a thermodynamic and kinetic standpoint. Thus, upon in vitro reduction, a glucosylated protein adduct is converted to a glucitollysine adduct and is "locked" into a conformation that differs chemically from the conformation of the Amadori rearrangement products. These features in the reductive glycosylation of a protein can be employed in the production of region specific antibodies.

The word "protein" is used herein to include proteinaceous materials that contain and are free from combined lipids. Thus, lipoproteins are included herein in the generalized meaning of the word protein, unless specifically excluded therefrom.

A protein according to the present invention can be modified by a hapten. The word "hapten", as used herein, means a substance having a chemical configuration such that it can interact with specific binding groups on an antibody, but which, unlike an antigenic determinant, does not itself elicit the formation of a detectable amount of antibody. When coupled with a protein, a hapten can elicit an immune response. A hapten according to the present invention can have a mass up to about 800–1000 daltons and, for example, can include about 4 or 5 linked monosaccharide units or about 10 linked amino acid residues.

The word "soluble", as used in conjunction with entities that are described as being capable of dissolution in water, is also used herein to include those entities that are dispersible in water.

The word "homologous" as used in the description of proteins is used herein in its usual sense to mean a protein from the same animal species as the species of the host. The word "autologous" is also used herein in its usual sense to mean a protein obtained from the same animal into which it is later introduced.

Homologous and autologous proteins are sometimes described herein as "self" proteins and are non-immunogenic in host animals. Heterologous proteins from species other than that of the host into which they are introduced are sometimes referred to herein as "non-self" proteins and are immunogenic when introduced into host animals.

The word "receptor" is used herein to mean an antibody in substantially pure form such as in ascites fluid or serum of an immunized animal or the idiotype-containing polyamide portion of an antioody in substantially pure form. Receptors useful herein bind at least with an antigenic molecule when admixed therewith in aqueous solution, at least at physiological pH values and ionic strengths. Preferably, the receptors also bind to an antigenic molecule within a pH value range of about 5 to about 9, and at ionic strengths such as that of distilled water to that of about one molar sodium chloride.

Idiotype-containing polyamide portions of antibodies are those portions of antibodies that bind to the epitope of the antigenic molecule. Such portions include the Fab, Fab', and F(ab')$_2$ fragments prepared from antibodies by well-known enzymatic cleavage techniques. Inasmuch as the antibodies from which idiotype-containing polyamides are obtained are described as raised against or induced by immunogens, idiotype-containing polyamide receptors will also b discussed as being "raised" or "induced" with the understanding that a cleavage step is required to obtain an idiotype-containing polyamide from an antibody.

Receptors that comprise the epitope-specific reagents of this invention can be raised by immunization of chemically modified self proteins. Such receptors are normally considered to be polyclonal since a whole protein containing a plurality of epitopes is used for immunizations. However, because substantially all of the self protein, except for the sites of chemical modification by a hapten (epitopes), is non-immunogenic in the host animals, the receptors so raised are surprisingly narrow in their binding specificities, and those binding specificities are limited substantially to the sites of modification.

Receptors raised to modified self proteins will nevertheless be referred to herein as polyclonal with the understanding that the polyclonicity observed with such receptors is narrowed considerably from that usually observed when a non-self protein is used for immunization. The preparation of polyclonal receptors to immunogenic, hapten-modified, self proteins is discussed hereinafter as part of the production of monoclonal receptors.

The receptors can also be monoclonal, and monoclonal receptors such as antibodies are particularly preferred for use as epitope-specific reagents. The preparation of monoclonal antibody receptors is disclosed hereinafter.

In its broadest sense, the present invention contemplates an epitope-specific reagent. That reagent comprises a receptor raised in a host animal to an immunogenic protein that itself comprises a hapten-modified protein that is a homologous or autologous (self) protein as to the host animal and is non-immunogenic in the host as an unmodified, homologous or autologous protein. The receptor of this invention binds to the hapten-modified protein to form a binding complex but does not bind to the unmodified protein.

Thus, the epitope-specific reagent of this invention is a result of immunization with a self protein that is itself not immunogenic in the host, but that is immunogenic after modification. The production of such receptors is contrary to the usually expressed dogma of immunology which suggests that self proteins are not immunogenic.

The receptors of the present invention must also be distinguished from previously prepared receptors that were raised to a heterologous protein modified by a hapten. Those receptors typically were of low avidity as to the site of hapten modification and most of the antibodies were raised against the non-self, large protein molecule carrier.

It is thus believed that the receptors of this invention that are specific to the sites of modification of self molecules are the first receptors raised against or to, or induced by an immunogen which is a modified homologous or autologous protein, wherein the homologous or autologous (self) protein acts as a carrier and the modifying entity is the specific immunogen to which the receptors bind.

The present invention further contemplates a method of preparing a receptor of this invention, a method of assaying using such a receptor and a diagnostic system that includes a receptor of this invention in packaged form. The following discussion describes several embodiments of the present invention with emphasis on particularly preferred monoclonal antibody receptors, their preparation and use as exemplary of the more general invention.

II. Materials and Methods

A. Lipoprotein Isolation and Characterization

Human plasma lipoproteins were isolated from pooled fresh plasma that was obtained from fasting normal healthy donors by plasmapheresis. Pools comprising the plasma of three or more donors were used. Plasmapheresis is a procedure in which red blood cells are separated from the plasma of a blood donor and returned to the circulatory system of the donor. The procedure can be done for purposes of collecting plasma components or for therapeutic purposes.

A low density lipoprotein fraction (LDL) having a density from about 1.019 to 1.063 grams per milliliter, and a high density lipoprotein fraction (HDL) having a density from about 1.063 to 1.5 grams per milliliter were isolated by sequential ultracentrifugation using solid potassium bromide (KBr) for density adjustment in the presence of 0.1 percent (weight per volume) ethylenediaminetetracetic acid (EDTA), 1 milligram per milliliter gentamycin sulfate, 0.2 percent sodium azide ($NaN_3$), 1 millimolar benzamidine, 10 millimolar diisopropylfluorophosphate and 10 micrograms per milliliter soybean trypsin inhibitor as described in greater detail in Curtiss et al., *J. Biol. Chem.*, 257, 15213 (1982), which is incorporated herein by reference.

The lipoprotein fractions were dialyzed thoroughly against a lipoprotein buffer containing 0.15 molar sodium chloride (NaCl), 0.3 millimolar EDTA, 5 millimolar benzamidine and 0.005 percent alpha-tocopherol, at pH 7.4. The resulting lipoprotein-containing solutions were filter-sterilized and stored at 4 degrees C for no more than 14 days.

The total protein content of the lipoproteins was analyzed according to the procedure described in Markwell et al., *Anal. Biochem.*, 87, 206 (1978) which is a modification of the method of Lowry et al. [*J. Biol. Chem.* 193, 265 (1951)]using a bovine serum albumin (BSA) standard. All lipoprotein concentrations are expressed on the basis of protein. The purity and apoprotein composition of each lipoprotein fraction was assessed by sodium dodecyl sulfate-polyacrylamide gel electrophoresis (SDS-PAGE) as outlined below.

Murine LDL, obtained from female Balb/c mice on a normal diet, was isolated from 50 milliliters of pooled plasma, and was extensively dialyzed against phosphate-buffered saline (PBS) containing 1 millimolar EDTA. The resulting solution was then sterilized.

B. Preparation and Characterization of Glucosylated Proteins and Compounds

The reaction scheme for the non-enzymatic glucosylation of a protein is shown in FIG. 1. Glucose forms a labile Schiff base intermediate with the epsilon amino group of lysine [Witztum et al., *Diabetes*, 31, 382 (1982) and Schleicher et al., *FEBS Lett.*, 129, 1 (1981)], which in the absence of a reducing agent undergoes an Amadori rearrangement to form a relatively stable ketoamine [Means et al., *Diabetes*, 31 (Suppl. 3), 1, (1982) and Higgins et al., *J. Biol. Chem.*, 256, 5204 (1981)]. As a result, a bulky glyco group is added to a lysine residue of the protein. The ketoamine in turn exists in equilibrium with a hemiketal or ring form (specifically, deoxyfructosyl-lysine).

When glucosylation is carried out in vitro in the presence of a reducing agent, the labile Schiff base is immediately and quantitatively reduced to glucitollysine [Higgins et al., supra]. Thus, the reduced form of a glucosylated protein is not chemically equivalent to the non-reduced, Amadori rearrangement products which are formed in vivo.

Proteins that were glucosylated in the presence of glucose and a reducing agent, such as sodium borohydride ($NaBH_4$) or sodium cyanoborohydride ($NaCNBH_3$), are referred to herein as reduced glucosylated protein adducts [glc(RED)-protein adducts or simply glc(RED)-protein]; whereas proteins that were glucosylated in the absence of a reducing agent (the Amadori rearrangement products) are referred to as non-reduced glucosylated protein adducts [glc(NR)-protein adducts.]

It should be pointed out that when a glc(NR)-protein adduct is reduced with sodium borohydride, mannositol-lysine is formed in addition to glucitollysine because the $C_2$ carbon can epimerize during the reduction reaction. Reduction of the Schiff base with sodium cyanoborohydride, however, typically yields only glucitollysine.

Murine glc(RED)-LDL was prepared by incubating 2 milligrams of murine LDL at room temperature (23 degrees C.) for 7 days in 5 milliliters of sterile PBS, pH 7.4, containing 80 millimolar glucose (Mallinckrodt Chem. Co., St. Louis, Missouri) and 12.5 milligrams per milliliter of fresh sodium cyanoborohydride (J.T. Baker Chem. Co., Phillipsburg, N.J.). Reduced (or non-reduced) forms of human glucosylated LDL and glucosylated HDL were prepared by incubating 5 milligrams of protein for 3 to 168 hours at 37 degrees C. in 2 to 5 milliliters of sterile PBS, pH 7.4, containing 80 millimolar glucose in the presence (or absence) of 12.5 milligrams per milliliter sodium cyanoborohydride.

In separate trials, Polylysine-4000, human albumin, transferrin and hemoglobin (Sigma Chemical Co., St. Louis, Missouri) were glucosylated in a manner similar to the above procedure. Reduced mannosylated LDL (man(RED)-LDL) was also prepared in manner similar to the above procedure, but with substitution of 80 millimolar mannose (Mallinckrodt Chem. Co., St. Louis, Missouri) for glucose.

At the end of the incubations, all samples were exhaustively dialyzed against PBS and were sterilized. The extent of glucosylation of each of the samples was assessed by amino acid analysis according to the procedure described in Witztum et al., *Diabetes*, 31, 382 (1982). Glucitollysine was synthesized according to the method of Schwartz et al., *Arch. Biochem. Biophys.*, 181, 542 (1977) using alpha-tertiary-butoxycarbonyl-lysine (Vega Biochemical, Tuscon, Arizona) as described in Witztum et al., supra.

C. Immunization

Two 16 week old female Balb/c mice were each injected intraperitoneally with 20 micrograms of murine glc(RED)-LDL emulsified in complete Freund's adjuvant. On days 14 and 28, each mouse received secondary intraperitoneal injections of 20 micrograms of murine glc(RED)-LDL in incomplete Freund's adjuvant. It has been demonstrated that apoprotein B of human LDL is a good immunogen in Balb/c mice [Curtiss et al., supra. and Tsao et al., *J. Biol. Chem.*, 257, 15222 (1982)]. Therefore, to prevent an antibody responce in the immunized mice to normal non-glucosylated epitopes on human LDL; homologous Balb/c LDL was glucosylated in the presence of sodium cyanoborohydride and was used as the primary and secondary immunogen.

Four days before fusion (day 51) the mice were given intravenous injections of 20 micrograms of human glc(RED)-LDL having 46 percent of lysines glucosylated to enhance the in vivo proliferative expansion and differentation of murine B cell clones producing antibodies that were capable of crossreacting with human glc(RED)-LDL. Mice were bled on days 0, 38, and 55 and the serum antibody responses for human glc(RED)-LDL, the prefusion immunogen, were monitored by solid phase radioimmunoassay (RIA) at serum dilutions of greater than $10^{-6}$ as described below.

Figure 2:
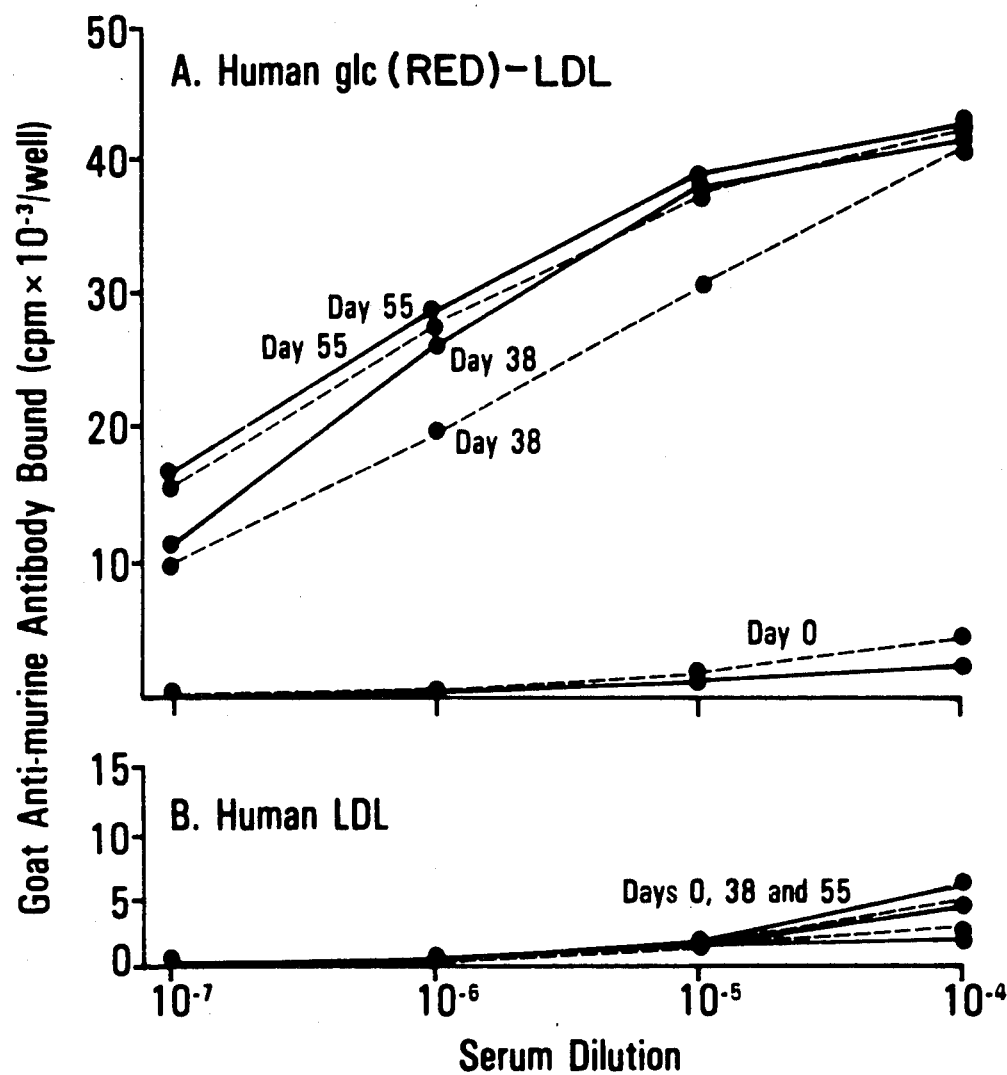
FIG. 2 illustrates the level of serum antibody reactivity against reduced human glucosylated LDL (glc(RED)-LDL) and human LDL in each of two immunized mice after 0, 38, and 55 days as determined by solid phase radioimmunoassay. Solid and dashed lines are used respectively to represent each of the two mice.

In particular, with reference to FIG. 2, no response to (non-glucosylated) normal human LDL could be detected in the sera of the immunized mice. Thus, the immune spleen cells used for fusion contained a highly restricted population of antigen specific antibody forming B cells. This was confirmed when these spleen cells were fused in vitro with mouse myeloma cells, as will be described, in the presence of a fusion promoter and the fused cells were plated out in culture plates. Of the 768 hybridoma cell cultures originally plated out, 187 contained hybridomas that produced antibody capable of binding human glc(RED)-LDL. Of these 187 culture supernatants, 176 (94 percent) did not react with normal human LDL. Six hybridomas from this fusion were cloned and propogated for use in the present invention.

D. Generation of Monoclonal Antibodies

The spleens of the two mice were removed, suspended in complete HT medium containing 0.1 millimolar azaguanine (Kennett et al., Curr. Top. Microbiol. Immunol., 81, 77 (1978), pooled to yield $3.2 \times 10^8$ total cells, and fused with P3×63Ag8.653 mouse myeloma cells in the presence of a fusion promoter [e.g., 30 percent (weight per volume) polyethylene glycol-1000 (PEG 1000), a commercially available fusion promoter having an average molecular weight from about 1000 to about 4000] at a ratio of 10 myeloma cells per spleen cell as described in Curtiss et al., supra.

According to accepted practices, the mouse myeloma cell line should preferably be of the "drug resistant" type, so that unfused myeloma cells will not survive in a selective medium, while hybrids will survive. The most common class is 8-azaguanine resistant cell lines, which lack the enzyme hypoxanthine guanine phosphoribosyl transferase and thus will not be supported by HAT (hypoxanthine, aminopterin and thymidine medium).

Three days after fusion, viable cells were plated out in 96-well tissue culture plates at $2 \times 10^4$ viable cells per well (768 total wells) in HAT medium (Kennett et al., supra) the cells were fed seven days after fusion with HT media and at approximately 4-5 day intervals thereafter as needed. Growth was followed microscopically and culture supernatants that contained antibodies were collected on day 14 for assay of antigen-specific antibody production by solid phase radioimmunoassay (RIA). On day 14, 79.6 percent of the wells contained colonies of viable cels with 18.4 percent of those wells containing a single colony.

Of 611 wells assayed, 187 wells or 31 percent of the culture supernatants reacted with human glc(RED)-LDL. These 187 wells were selected for differential screening [i.e., no reaction with normal human LDL, but good reaction with human glc(RED)-LDL]; and 6 were selected 21 days after fusion for recloning by limiting dilution in which the volume of diluent is statistically calculated to isolate a certain number of cells (e.g., 1-4) in each separate container (e.g., each well of a microtiter plate). Cloned hybridomas were cultivated in a medium containing 10 percent calf serum and were stored frozen in liquid nitrogen as described by Kennedy et al., Diabetes, 31 (Suppl. 3), 52 (1982).

Once the desired hybridoma has been selected and cloned, the resultant antibody may be produced in one of two ways. The more pure monoclonal antibody is produced by in vitro culturing of the desired hybridoma in a suitable medium for a suitable length of time, followed by recovery of the desired antibody from the supernatant. The suitable medium and length of culturing time are known or are readily determined. The in vitro technique produces essentially monospecific monoclonal antibody that is substantially free from other specific antihuman immune globulin. There is a small amount of other immune globulin present since the medium contains xenogenous serum (e.g., fetal calf serum). However, this in vitro method may not produce a sufficient quantity or concentration of antibody for some purposes.

To produce a much greater concentration of slightly less pure monoclonal antibody, the desired hybridoma can be injected into mice, preferably syngenic or semi-syngenic mice. The hybridoma will cause formation of antibody-producing tumors after a suitable incubation time, which will result in a relatively high concentration of the desired antibody in the bloodstream and peritoneal exudate (ascites) of the host mouse. Although these host mice also have normal antibodies in their blood and ascites, the concentration of these normal antibodies is only about 5 percent of the monoclonal antibody concentration. Moreover, since these normal antibodies are not antihuman in their specificity, the monoclonal antibody obtained from the harvested ascites or from the serum is essentially free of any contaminant antihuman immune globulin.

Immunoglubolin heavy and light chains of the antibodies secreted by the cloned hybridomas were typed using the Mono AB-ID EIA Kit A (lot Number 20920, Zymed Labs Inc., San Francisco, California). The assays were performed with hybridoma culture supernatants as described by the manufacturer.

The hybridomas were given the following designations for reference purposes and were deposited with the American Type Culture Collection, Rockville, Maryland under the following ATCC CRL accession numbers.

| Hybridoma | Subclone | ATCC CRL Accession No. |
|---|---|---|
| G5H3 | 2C4.6D11 | HB 8355 |
| G6C9 | IC87G11 | HB 8356 |
| G8C11 | 3H3.8D8 | HB 8357 |
| G5E10 | 2A510H11 | HB 8359 |
| G8H6 | 2A1.5G8 | HB 8358 |
| G8G7 | 3G6.3G2 | HB 8354 |

The above ATCC deposits will be maintained in an unrestricted form until the end of the duration of a patent granted on this application provided, of course, a patent is granted on this application, and thus the above hybridomas will be available to any third party according to accepted ATCC practices.

E. Solid Phase Radioimmunoassay

Assays were performed in flexible round bottom polyvinyl chloride microtiter plates (Falcon, Micro Test III, Becton Dickinson and Co., Oxnard, California). The wells were coated with lipoprotein antigens by adding 0.05 milliliters of lipoprotein in PBS or lipoprotein buffer and incubating the plates for 3 hours at room temperature to give a constant final bound antigen concentration. All antigens were coated at 1 microgram per milliliter. The wells were "post-coated" for 30 minutes with 0.25 milliliters of PBS containing 3 percent bovine serum albumin (BSA) and 3 percent normal goat serum to block the remaining active sites. For assay, 0.05 milliliter of mouse serum or hybridoma culture supernatant, diluted in PBS containing 3 percent bovine albumin, 3 percent goat serum and 0.05 percent polyoxyethylene (20) sorbitan monolaurate (TWEEN-20) were added and incubated for 18 hours at 4 degrees C.

reduced Amadori adducts of the glucosylation reaction [glc(NR)-LDL]. In contrast to the normal apoprotein B-specific antibody (B24), each of the antibodies from this fusion as indicated in Table 1 reacted only with glc(RED)-LDL, and none of them reacted with either normal LDL or glc(NR)-LDL.

TABLE 1

SPECIFICITY OF THE CLONED HYBRIDOMA CULTURE SUPERNATANTS FOR glc(RED)-LDL[1]

| Monoclonal Antibody | Ig Type[2] | Mean $^{125}$I—Goat Anti-murine Ig Bound[1] (cpm/well) | | | |
|---|---|---|---|---|---|
| | | glc(RED)-LDL | glc(NR)-LDL | LDL | Albumin |
| G5H3 | IgG$_1$k | 20,512 | 237 | 230 | 349 |
| G6C9 | IgG$_1$k | 15,750 | 471 | 287 | 445 |
| G8C11 | IgG$_1$k | 20,721 | 236 | 213 | 357 |
| G5E10 | IgG$_1$k | 21,299 | 262 | 267 | 501 |
| G8H6 | IgG$_1$k | 17,070 | 218 | 219 | 330 |
| G8G7 | IgMk | 20,434 | 240 | 268 | 287 |
| B24 | IgG$_1$k | 9,042 | 10,681 | 11,454 | 394 |
| AV45B6 | IgG$_1$k | 773 | 455 | 918 | 16,615 |

[1]All antigens were human proteins and were coated onto microtiter wells at a concentration of 1 microgram per milliliter. 46 Percent and 5.9 percent of the lysine residues of glc(RED)-LDL and glc(NR)-LDL, respectively, contained glucose as determined by amino acid analysis. All hybridoma culture supernatants were used at a dilution of 1:50 with PBS.
[2]The immunoglobulin heavy and light chains were determined as described herein.

After washing, mouse antibody binding was detected by a 4 hour incubation at 4 degrees C. with 10 nanograms per well of immunochemically purified and radioiodinated goat anti-murine immunoglubulin (3 to 4 microcuries per microgram) as described in Curtiss et al., supra.

Competitive assays were performed in an identical manner and contained 0.025 milliliters of competitor diluted in PBS containing 3 percent bovine serum albumin, 3 percent goat serum and 0.05 percent TWEEN-20, and 0.025 milliliters of culture supernatants containing limiting amounts of monoclonal antibody. Nonspecific binding was determined by replacing specific hybridoma culture supernatants with similar dilutions of the culture supernatants of non-related hybridomas producing immunoglobulins of the same heavy chain type.

The maximum amount of $^{125}$I-second antibody bound by specific antibody ($B_o$) was determined in the absence of competitors. Data was calculated as $B/B_o$ where B represents the mean counts per minute of antibody bound at a given concentration of competitor. A control monoclonal antibody, B24, binds with high affinity to the apoprotein of human LDL (apoprotein B) and has been extensively characterized. See Curtiss et al., supra and Tsao et al., supra]. An additional control monoclonal antibody, AV45B6, which binds human albumin, was obtained from the fusion of immune spleen cell with the SP 2/0 myeloma, and was found to be a class G subclass 2b immunoglobulin (IgG$_{2b}$) antibody.

F. Antibody Specificity

The specificity of the antibodies produced by the six cloned hybridomas was tested, and compared with two control mouse monoclonal antibodies obtained from other fusions (see Table 1). One of the controls, the B24 antibody, is an apoprotein B-specific antibody with a high affinity for human LDL [Curtiss et al., supra and Tsao et al., supra]. The second control, AV45B6, reacts specifically with human albumin. Using solid phase RIA, culture supernatants from the 6 cloned hybridomas were tested for their ability to react with the following human antigens bound to the microtiter plate: albumin, LDL, the glc(RED)-LDL antigen used for prefusion immunization and for screening, and the non- To determine if the inability of these antibodies to bind glc(NR)-LDL reflected only the low degree of glucosylation of lysine residues (5.9 percent for glc(NR)-LDL compared with 46 percent for glc(RED)-LDL), glc(RED)-LDL preparations containing between 3.3 percent and 28.9 percent of the total lysine residues modified, as assessed by amino acid composition analysis, were made. These preparations of glc(RED)-LDL were generated by incubating LDL with glucose in the presence of sodium cyanoborohydride for 3 to 75 hours. Each of these preprations of glc(RED)-LDL, as well as a preparation of LDL incubated for 75 hours with sodium cyanoborohydride in the absence of glucose, were compared in a solid phase RIA for their ability to compete with heavily glucosylated glc(RED)-LDL for antibody binding. All preparations of glc(RED)-LDL were able to compete with the glc(RED)-LDL (49.5 percent of lysines glucosylated) antigen bound to the plate for binding to each of the six monoclonal antibodies.

Figure 3:
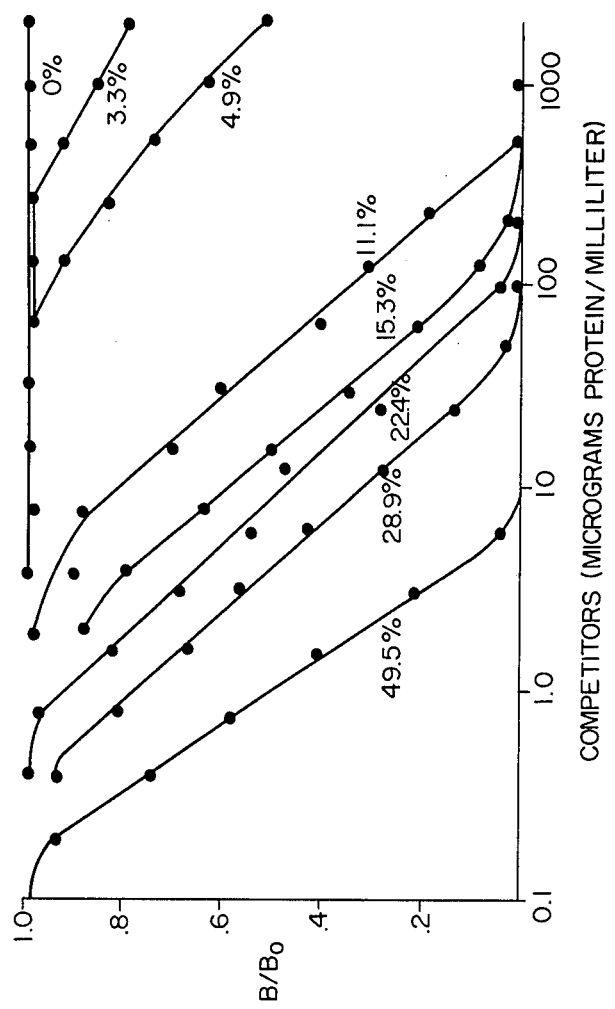
FIG. 3 illustrates the ability of various percent lysine-glucosylated and reduced LDL (ranging from 0 to 49.5 percent glucosylated) to compete with 49.5 percent lysine-glucosylated and reduced LDL for the binding of G5H3 monoclonal antibody at 1:800 dilution. The data qualitatively represent the results obtained with all six of the monoclonal antibodies used herein. The ordinate of the graph $[B/B_o]$ represents the fraction of bound antibody with the competitor present as compared to that fraction of antibody bound in the absence of competitor. The data were obtained by competitive double antibody radioimmunoassay.

Data obtained with the G5H3 antibody were representative of that obtained with the six monoclonal antibodies and are shown in FIG. 3. In all cases the degree of competition was directly related to the degree of glucosylation, and was independent of the LDL protein added. LDL incubated for 75 hours with sodium cyanoborohydride in the absence of glucose did not compete with any of these antibodies. Therefore, these antibodies bound a new epitope on LDL that was created by in vitro glucosylation and reduction, and could bind glc(RED)-LDL that contained as few as 3.3 percent of the lysines residues reductively glucosylated.

Figure 4:
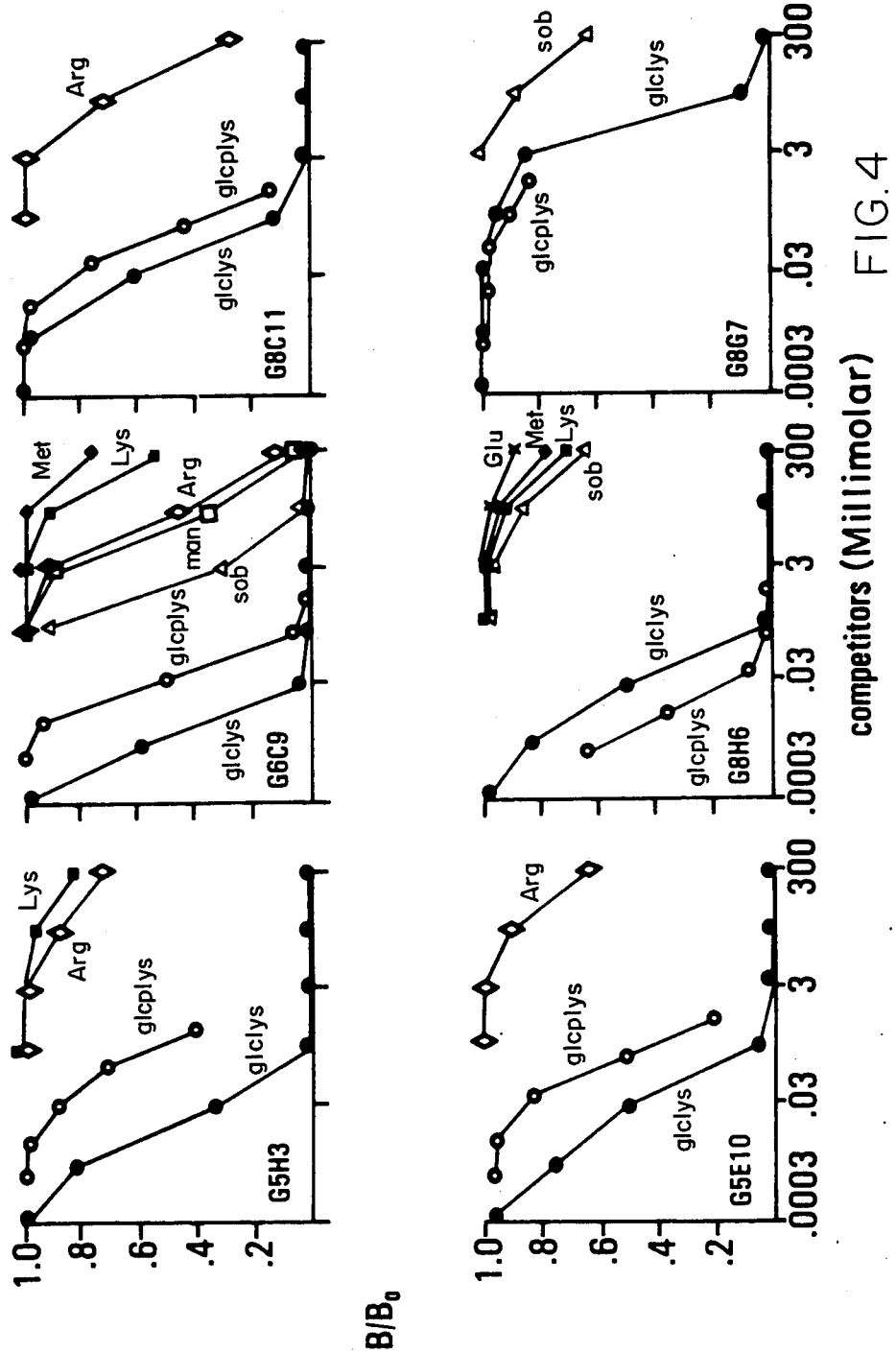
FIG. 4 illustrates the specificity of each monoclonal antibody (G5H3, G6C9, G8C11, G5E10, G8H6 and G8G7) for the following compounds as determined by the ability of each compound to compete with glc(RED)-LDL (48.7 percent lysines glucosylated) for the binding site of the antibody: (glclys) glucitollysine ( ), (glcplys) glucitolpolylysine ( ) glucose (not shown), mannose (not shown), (sob) sorbitol ( ), (man) mannitol (□), (Lys) lysine ( ), (Arg) arginine ( ), (Gln) glutamine (x), and methionined(met ( ). Only those compounds which were able to compete with glc(RED)-LDL for the binding site are illustrated. Data were obtained using a competitive double antibody RIA in which $^{125}$I-goat antimurine antibody was incubated for 4 hours at 4 degrees C. The following dilutions of mouse monoclonal antibody were used in the assay: G5H3 1:900, G6C9 1:1000, G8C11 1:900, G5E10 1:1000, G8H6 1:500 and G8G7 1:800.

The above data indicate that these antibodies reacted with the reduced glucose adducts of lysine conjugates (glucitollysine), but not with the non-reduced glucose adducts (ketoamine or hemiketal forms) (FIG. 1). To further define the specificity of the epitope identified by these antibodies, glucitollysine was synthesized and its ability to compete with glc(RED)-LDL for binding to each of the antibodies was determined. As shown in FIG. 4, glucitollysine could completely inhibit the binding of each of these antibodies. Glucitolpolylysine was prepared and was also found to be an effective competitor for each antibody. Thus, the reduced conjugate of glucose and lysine could occupy the antigen binding sites of each of these antibodies.

Next, the ability of a number of other simple compounds to compete in the RIA was determined. Those results are summarized in Table 2 which lists as competitors the amino acids: lysine, arginine, methionine and glutamine; the aldosehexose epimers: glucose and mannose; the hexose alcohol epimers; sorbitol (glucitol) and mannitol; and the reduced conjugate of glucose coupled to the epsilon amino group of lysine or polylysine (glucitollysine and glucitolpolylysine, respectively).

TABLE 2

| REACTIVITY WITH MONOCLONAL ANTIBODIES | | | | | | |
|---|---|---|---|---|---|---|
| Competitor | G5H3 | G6C9 | G8C11 | G5E10 | G8H6 | G8G7 |
| glclys | * | * | * | * | * | * |
| glcplys | * | * | * | * | * | * |
| Arg | * | * | * | * | — | — |
| Lys | * | * | — | — | * | — |
| Met | — | * | — | — | * | — |
| sob | — | * | — | — | * | * |
| man | — | * | — | — | — | — |
| Gln | — | — | — | — | * | — |
| glu | — | — | — | — | — | — |

List of Abbreviations
glclys = glucitollysine
glcplys = glucitolpolylysine
Arg = arginine
Lys = lysine
Met = methionine
sob = sorbitol
man = mannitol
Gln = glutamine
glu = glucose
The notation "*" indicates a positive reactivity.
The notation "—" indicates no measurable reactivity.

Since each of these compounds was to be added as a competitor at a fairly high concentration, each compound was first screened for non-specific effects by measuring the binding of antibody B24 (which is directed against native human apoprotein B) to glc(RED)-LDL coated plates in the presence of each of these compounds. This antibody fully recognized glc(RED)-LDL, i.e., glucosylation did not interfere with the apoprotein B epitope recognized by B24 (see Table 1). With the exception of lysine and arginine, none of the compounds were able to inhibit the binding of this antibody to glc(RED)-LDL at concentrations up to 300 millimolar (mM). The levels of inhibition produced by lysine (20 percent at 300 mM) and arginine (20 percent at 100 mM) were considered to be "non-specific" and only values which exceeded these levels were considered significant in the competitions performed with the glc(RED)-LDL-specific antibodies.

The ability of the 10 compounds to compete with glc(RED)-LDL for binding to each of the antibodies is shown in FIG. 4. Glucitollysine and glucitolpolylysine were effective competitors for each of the antibodies, whereas 300 mM amounts of glucose or mannose (not shown) did not compete with any of these antibodies. Since neither glucose nor mannose competed for binding to any of the antibodies, the hemiketal or ring from of the hexoses could not occupy the antigen binding site of any of these antibodies.

However, the glucose alcohol, sorbitol (glucitol), competed for binding to antibodies G8H6 and G8G7 at concentrations of greater than or equal to 300 mM and was a good competitor of antibody G6C9 (50 percent inhibition of 1 mM). Therefore, the open-chain hexose alcohol was able to occupy the antigen binding site of three of these antibodies. The observation that mannitol, the alcohol of mannose, could compete for binding to antibody G6C9, and was equally effective at a 10-fold higher concentration relative to sorbitol, suggests a relaxed specificity of this antibody for this epimer of sorbitol.

At least one of the amino acids, lysine or arginine, was able to significantly compete for all antibodies except G8G7. Only arginine competed for G8C11 and G5E10, whereas both amino acids competed for antibodies G6C9 and G5H3. Arginine was the most effective amino acid competitor of G6C9 and was able to inhibit binding by 50 percent at 20 mM, compared with lysine which required 300 mM for 50 percent inhibition. Lysine, but not arginine, significantly inhibited antibody G8H6; and this antibody, unlike all the others, was also inhibited by high concentrations of methionine and glutamine. Thus, the amino acid portion of glucitollysine also contributed to the individual specificity of some of these antibodies.

Glc(RED)-LDL containing 48.7 percent of its lysine residues conjugated with glucose was also included in the competitive RIA shown in FIG. 4. When the antibodies were compared for their relative ability to quantitate the estimated number of glucitollysine residues per mole of glc(RED)-LDL, one antibody was quite good. This comparison was accomplished by assuming a protein molecular weight for glc(RED)-LDL of $6.5 \times 10^5$ and a glucitollysine/LDL molar ratio of 156.

As shown in Table 3, the smallest difference in the amount of glucitollysine and glucitollysine residues on glc(RED)-LDL required for 50 percent inhibition of antibody binding was obtained with antibody G6C9, and this difference was less than 3-fold.

TABLE 3

RELATIVE ABILITY OF EACH ANTIBODY TO MEASURE THE ESTIMATED NUMBER OF GLUCITOLLYSINE RESIDUES ON glc(RED)-LDL

| | Concentration of Competitor Required for 50% Inhibition of Binding | | |
|---|---|---|---|
| Monoclonal Antibody | glucitollysine[1] (Micromoles/Liter) | glucitollysine-LDL[2] (Micromoles/Liter) | Difference[3] |
| G5H3 | 10 | 1.4 | 0.93 |
| G6C9 | 3 | 1.1 | 0.28 |
| G8C11 | 100 | 1.8 | 1.99 |
| G5E10 | 10 | 2.2 | 0.89 |
| G8H6 | 30 | 1.1 | 1.46 |
| G8G7 | 10,000 | 12.1 | 4.00 |

[1]Quantitated directly from the competitive RIA data shown in FIG. 4.
[2]Estimated from the competitive RIA data shown in FIG. 4. Glc(NR)-LDL was added as competitor to this assay at concentrations of 0.3–50 micrograms/milliliter. The micromolar concentration of glucitollysine on glc(RED)-LDL was calculated using an LDL protein molecular weight of $6.5 \times 10^5$, and an estimated 320 lysine residues per mole of LDL [Gonen et al., Diabetes, 30, 875 (1981)]. Amino acid composition analysis of this preparation of glc(RED)-LDL indicated that 48.7 percent of the lysine residues were glucitollysine.
[3]$\log_{10}$ of the difference between the concentration of glucitollysine (micromoles/liter) required for 50 percent inhibition and the concentration of glucitollysine residues on LDL (micromoles/liter) required for 50 percent inhibition.

Reductively mannosylated LDL was also prepared by incubating LDL with mannose in the presence of sodium cyanoborohydride. Mannosylated LDL [man(-RED)-LDL](79 percent of lysines mannosylated) was a poor competitor for the binding of each of the antibodies to glc(RED)-LDL (49.5 percent of lysines glucosylated) and greater than 1000 times more man(RED)-LDL protein was required for comparable levels of inhibition (see FIG. 5). Thus, each of the antibodies also displayed a striking degree of specificity for the glucose epimer conjugate of LDL.

G. Identification of Glucitollysine Residues In Other Isolated Proteins

The observation that glucitollysine is a dominant determinant of the epitope recognized by each of these antibodies suggested that these antibodies could be used to quantitate this residue in other isolated proteins. Competitive RIA was used to identify reductively glucosylated human HDL, albumin, transferrin and hemoglobin.

Figure 5:
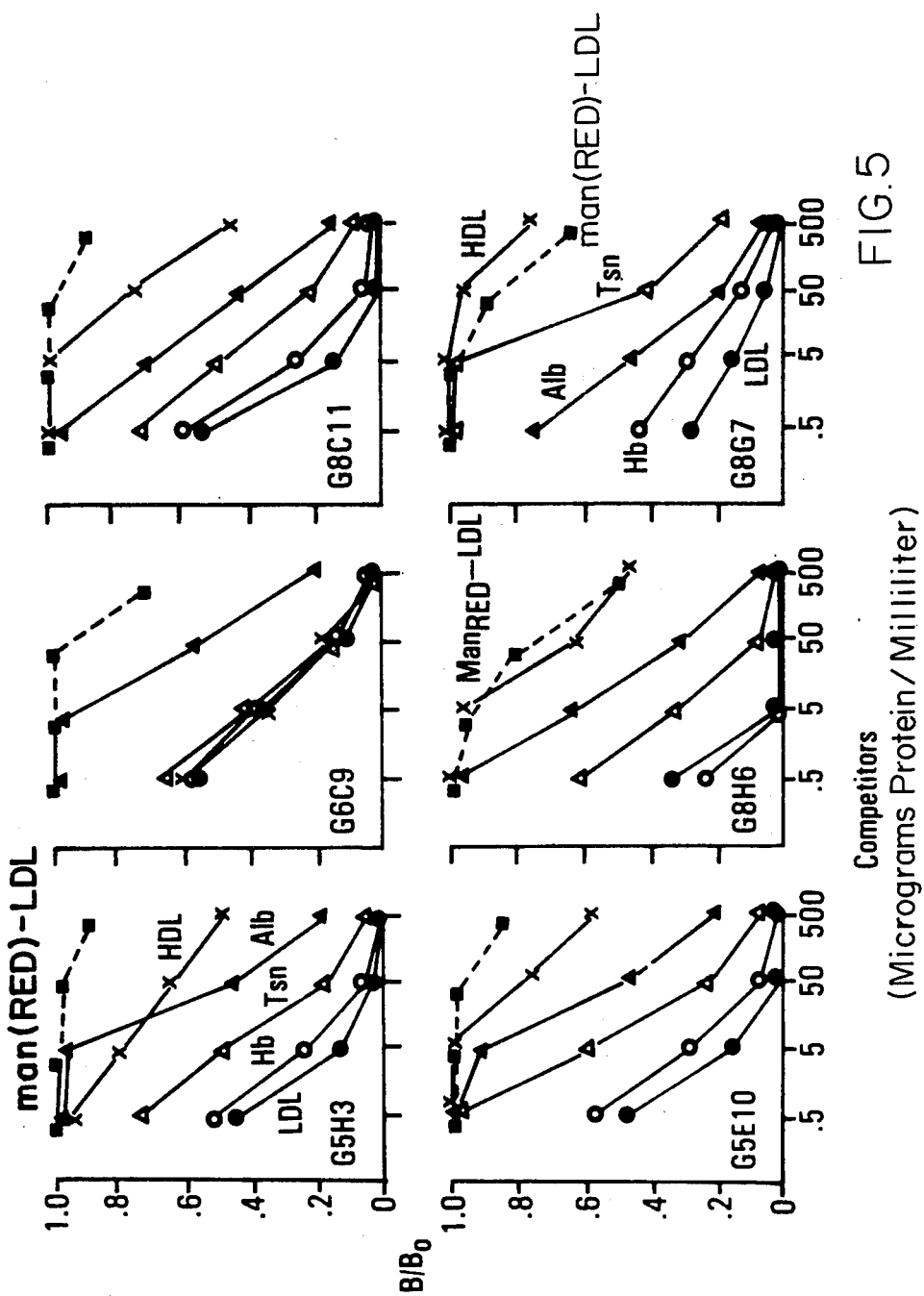
FIG. 5 illustrates the use of monoclonal antibodies (G5H3, G6C9, G8C11, G5E10, G8H6 and G8G7) to identify reduced glucosylated epitopes on human plasma proteins [LDL, HDL, hemoglobin (Hb), albumin (Alb) and transferrin (Tsn) and reduced mannosylated epitopes on human LDL [man(RED)-LDL]. The identification of the epitopes was accomplished by determining the ability of the protein to compete with glc(RED)-LDL (49.5 percent lysine glucosylated) for the binding site of the antibody in a competitive double antibody RIA.

Referring now to FIG. 5, each of these proteins competed for binding to each of the six monoclonal antibodies. Whereas the amount of each glc(RED)-protein required for comparable levels of inhibition differed, each did compete to some extent. In contrast, the same proteins glucosylated in the absence of a reducing agent (glc(NR)-protein adducts) failed to compete with glc(RED)-LDL for binding to any of the monoclonals, despite the fact that they all contained at least 6 percent of their lysine residues conjugated to glucose in the Amadori forms (data not shown).

Moreover, evidence concerning the specificity of the individual antigen combining sites of each antibody was obtained from these competitive assays. As illustrated in FIG. 5, different quantitative differences in binding were observed among the six different antibodies. For example: (a) glc(RED)-hemoglobin was a better competitor than glc(RED)-LDL in competing for binding of antibody G8H6; (b) glc(RED)-albumin was a better competitor than glc(RED)-transferrin for all antibodies except G8G7; and (c) all the glc(RED)-protein adducts except albumin were equally good competitors for binding to only antibody G6C9.

H. Identification Of Glucitollysine Residues In Plasma Proteins of Control and Diabetic Subjects The above data demonstrate that these monoclonal antibodies recognized only the reduced glucose adduct, glucitollysine. It is believed that most of the glucose adducts present in vivo are present only in an Amadori rearrangement form [Goldstein et al., Diabetes, 31 (Suppl. 3), 70 (1982)]. If this is true, non-reduced glucosylated plasma proteins from normal or diabetic subjects should have little reactivity with these monoclonal antibodies, whereas glucosylated plasma proteins subsequently reduced in vitro (post-reduced) should react. The specific reducing agent, sodium cyanoborohydride reduces Schiff base forms, but not the stable Amadori forms. Sodium borohydride, which is a more general reducing agent, converts both the Schiff base and the Amadori forms (see FIG. 1).

Thus, quantitation of glucitollysine residues of native plasma proteins measures the content of this adduct in plasma. Quantitation of glucitollysine residues in plasma proteins reduced with sodium cyanoborohydride subsequent to removal of free glucose determines the content of glucose adducts originally present in the Schiff base form. And quantitation of glucitollysine residues in plasma proteins reduced with sodium borohydride subsequent to the removal of glucose yields the content of total glucose adducts including the labile Schiff base and the Amadori rearrangement products.

Plasmas were initially obtained from seven individuals (designated A through G) to assess the ability of these antibodies to identify and quantitate these glucose adducts.

Blood was drawn into an EDTA-containing solution by venipuncture from seven subjects including normoglycemic controls and patients with diabetes mellitus requiring insulin therapy. The cells were removed by low speed centrifugation and the washed red blood cell lysates were assayed for glucosylated hemoglobin A using the Isolab column technique (Isolab, Inc., Akron, Ohio). Plasma glucose was determined by the glucose oxidase method [Witztum et al., Diabetes, 31, 382 (1982)].

The plasma was adjusted to 1 millimolar EDTA, clarified by centrifugation at 11,000xgravity at 4 degrees C. and immediately stored at minus 70 degrees C. To remove free glucose, 0.9 milliliters of plasma (clarified by centrifugation to remove cellular debris) was chromatographed on a 0.5 by 20 centimeter column of Sephadex G-25 (a beaded carbohydrate polymer supplied by Pharmacia Fine Chemicals, Piscataway, N.J.) equilibrated in PBS containing 1 millimolar EDTA. The void volume (4 milliliters) eluate was incubated at 37 degrees C. for four hours in the absence of a reducing agent, or in the presence of either 12 millimolar sodium cyanoborohydride or 10 millimolar sodium borohydride. After exhaustive dialysis against PBS at pH 7.2, plasma protein was determined as described by Markwell et al., supra. The plasmas were added as competitors (0.025 milliliters) to the solid phase RIA described above using human glc(RED)-LDL (48.7 percent lysines glucosylated) at 1 microgram per milliter for antigen coating, and glucitollysine at 0.1 to 300 micromole per milliliter as the standard.

Using glucitollysine as the standard in a competitive RIA, the moles of glucitollysine residues per milligram of plasma protein were quantitated using five of the six antibodies. The sixth antibody, G8G7, was not studied further, since it is an IgM antibody (Table 1), and was only inhibited by high concentrations of glucitollysine (Table 3).

Figure 6:
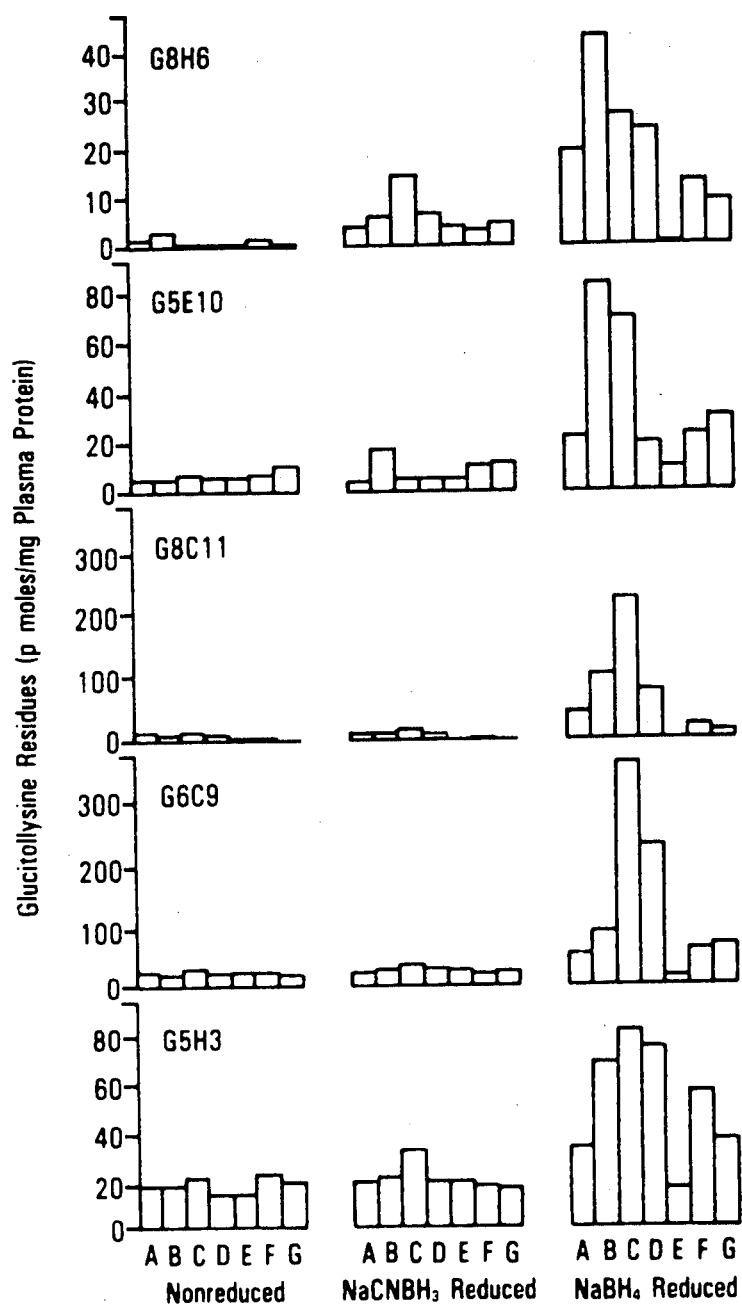
FIG. 6 illustrates the use of monoclonal antibodies to quantitate the extent of glucosylation of total plasma proteins and the state of the glucosylated residues (i.e., reduced, Schiff base, Amadori rearrangement product form) in normoglycemic individuals and hyperglycemic diabetic individuals. Each bar corresponds to one of seven individuals identified as A through G. Glucitollysine residues measured in the non-reduced plasma, sodium cyanoborohydride-reduced plasma and sodium borohydride-reduced plasma represent background, Schiff base forms and Schiff base plus Amadori rearrangement forms, respectively.

As expected, only very small amounts of glucitollysine were found in the seven individual native (nonreduced) plasmas (FIG. 6). However, while some of the antibodies were capable of identifying larger amounts of glucitollysine residues in the sodium cyanoborohydride-reduced pasmas of some of the subjects, each of them identified substantially more residues in the sodium borohydride-reduced plasmas. A comparison of the relative amounts of glucitollysine residues in the sodium cyanoborohydride-reduced plasma aliquots vs. the sodium borohydride-reduced aliquots indicates that the majority of the glycosylated proteins in plasma existed as the Amadori rearrangement products rather than in the more labile Schiff base form.

The number of glucitollysine residues quantitated in the sodium borohydride-reduced plasmas showed considerable variation among the seven individuals tested (FIG. 6). To determine if the level of detectable plasma glucitollysine residues was correlated with high plasma glucose and high HbA$_{IC}$ values, the sodium borohydride-reduced plasmas of normal (non-diabetic) individuals and patients with diabetes mellitus were assayed.

As shown in Table 4, the mean plasma glucose for five normal (non-diabetic) individuals and ten diabetic individuals was 79±11 milligrams per deciliter (mg/dl) and 245±113 mg/dl, respectively, and the mean HbA$_{IC}$ values for the same five normal and ten diabetic individuals were 6.8±0.4 percent and 11.2±2.0 percent, respectively.

TABLE 4

GLUCITOLLYSINE RESIDUES IN SODIUM BUROHYDRIDE (NaBH₄) REDUCED PLASMA

| Plasma Source | Plasma Glucose (mg/dl) | HbA$_{1C}$ (Percent) | Glucitollysine Residues (pico moles/mg protein)[1] | | | | |
|---|---|---|---|---|---|---|---|
| | | | G5H3 | G6C9 | G8C11 | G5E10 | G8H6 |
| Normal 1 | 91 | 7.3 | 34 | 60 | 42 | 23 | 20 |
| Normal 2 | 90 | 6.6 | 18 | 50 | 31 | 28 | 30 |
| Normal 3 | 67 | 6.3 | 17 | 43 | 36 | 22 | 22 |
| Normal 4 | 75 | 6.8 | 24 | 61 | 43 | 29 | 24 |
| Normal 5 | 71 | 6.8 | 17 | 50 | 30 | 22 | 25 |
| Mean ± S.D.[2] | 79 ± 11 | 6.8 ± 0.4 | 22 ± 7 | 53 ± 8 | 36 ± 6 | 25 ± 3 | 24 ± 4 |
| Diabetic 1 | 150 | n.d.[3] | 69 | 98 | 105 | 85 | 46 |
| Diabetic 2 | 301 | 12.6 | 82 | 360 | 228 | 72 | 34 |
| Diabetic 3 | 288 | 9.4 | 75 | 229 | 81 | 21 | 29 |
| Diabetic 4 | 113 | 8.7 | 58 | 65 | 35 | 24 | 15 |
| Diabetic 5 | 104 | n.d.[3] | 39 | 73 | 32 | 30 | 12 |
| Diabetic 6 | 136 | n.d.[3] | 47 | 186 | 136 | 84 | 87 |
| Diabetic 7 | 279 | 9.7 | 32 | 79 | 66 | 37 | 38 |
| Diabetic 8 | 437 | 12.2 | 60 | 160 | 192 | 96 | 65 |
| Diabetic 9 | 291 | 11.3 | 33 | 105 | 88 | 70 | 41 |
| Diabetic 10 | 349 | 14.4 | 47 | 206 | 135 | 77 | 47 |
| Mean ± S.D. | 245 ± 113 | 11.2 ± 2.0 | 54 ± 17 | 156 ± 93 | 110 ± 64 | 60 ± 28 | 41 ± 22 |

[1]Fasting plasmas, freed of glucose by chromatography, were incubated for 4 hours at 37° C. in the presence of 10 millimolar NaBH₄. Total plasma proteins were quantitated after dialysis against PBS, pH 7.4, and added to RIAs employing the five antibodies shown. Glc(RED)-LDL (48.7 percent of lysines glucosylated) was used for antigen coating and glucitollysine was used as the standard. Numbers shown represent the mean of quadruplicate determinations.
[2]S.D. = Standard deviation.
[3]n.d. = not determined.

Therefore, significant differences between the two groups were identified with respect to the concentration of plasma glucose and the percent of glycosylated Hb. Significant differences in the number of glucitollysine residues per milligram of NaBH₄-reduced plasma proteins also were detectable with each of the five antibodies (Table 4).

Even though the number of glucitollysine residues quantitated by each of the antibodies differed, each antibody was capable of identifying 2-to 8-fold increases in the number of glucitollysine residues in the NaBH₄-reduced plasma proteins of diabetics. Therefore, these antibodies are capable of identifying glucosylated plasma proteins, and these glucosylated proteins are increased in the plasma of patients with diabetes mellitus.

To demonstrate that these antibodies also could recognize glucitollysine residues in isolated lipoproteins, very low density (VLDL) plus intermediate density lipoproteins (IDL), LDL and HDL fractions were isolated from seven normal and 13 diabetic plasmas, and the glucitollysine residues were measured with antibody G6C9 (Table 5). The mean content of glucitollysine was almost 10-fold higher in the total plasma proteins of these diabetics, although their HbA$_{IC}$ was increased only 2.5-fold. There was an approximate 3- to 4-fold increase in glucitollysine content of diabetic LDL and HDL preparations, and an 8-fold increase in the glucitollysine residues in the isolated VLDL plus IDL fraction of the diabetics. Including normals and diabetics, the correlation coefficient between plasma glucose levels and total plasma glucitollysine content was $r = 0.834$ (p [significant value] less than 0.001), and of HbA$_{IC}$ and total plasma glucitollysine content was $r = 0.824$ (p less than 0.001). There were also significant correlations between plasma glucose and glucosylated VLDL plus IDL, and plasma glucose and glucosylated HDL of $r = 0.703$ (p less than 0.001) and $r = 0.818$ (p less than 0.001), respectively.

TABLE 5

GLUCITOLLYSINE RESIDUES IN NaBH₄ REDUCED PLASMA AND ISOLATED LIPOPROTEINS USING ANTIBODY G6C9

| Plasma Source | Plasma Glucose (Milligrams) (per deciliter) | HbA$_{1C}$ (Percent) | Glucitollysine Residues[1] | | | |
|---|---|---|---|---|---|---|
| | | | Plasma | VLDL + IDL | LDL | HDL |
| | | | (picomoles/milligram protein) | | | |
| Normal | | | | | | |
| 6 | 67 | 3.9 | 9 | 53 | <47[3] | 40 |
| 7 | 91 | 6.8 | 28 | 168 | <41 | 36 |
| 8 | 69 | 5.6 | 8 | 200 | <24 | 39 |
| 9 | 74 | 5.2 | 24 | ND[2] | <34 | 49 |
| 10 | 75 | 5.2 | 35 | 107 | <39 | 52 |
| 11 | 66 | 5.9 | 19 | ND | <29 | 39 |
| 12 | 86 | 5.9 | 32 | ND | <26 | 57 |
| Mean ± SD | 75 ± 10 | 5.5 ± 0.9 | 22 ± 11 | 132 ± 65 | <47 | 45 ± 8 |
| Diabetic | | | | | | |
| 11 | 222 | 10.1 | 196 | 268 | 67 | 101 |
| 12 | 286 | 14.4 | 285 | 1,450 | 118 | 133 |
| 13 | 314 | 12.5 | 181 | 2,323 | 53 | 96 |
| 14 | 275 | 15.3 | 92 | 969 | 53 | 241 |
| 15 | 238 | 8.5 | 56 | 241 | 193 | 87 |
| 16 | 303 | 13.9 | 136 | 724 | 243 | 142 |
| 17 | 245 | 15.8 | 201 | 1,304 | 65 | 172 |
| 18 | 299 | 13.9 | 432 | 2,088 | 136 | 254 |

TABLE 5-continued

GLUCITOLLYSINE RESIDUES IN NaBH$_4$ REDUCED PLASMA AND
ISOLATED LIPOPROTEINS USING ANTIBODY G6C9

| Plasma Source | Plasma Glucose (Milligrams) (per deciliter) | HbA$_{1C}$ (Percent) | Glucitollysine Residues[1] | | | |
|---|---|---|---|---|---|---|
| | | | Plasma | VLDL + IDL | LDL | HDL |
| | | | (picomoles/milligram protein) | | | |
| 19 | 271 | 11.3 | 174 | 1,173 | 190 | 155 |
| 20 | 320 | 15.5 | 320 | 794 | 106 | 381 |
| 21 | 276 | 15.4 | 329 | 1,049 | 102 | 211 |
| 22 | 396 | 16.3 | 432 | 1,001 | 180 | 361 |
| 23 | 110 | —[4] | 49 | 222 | 43 | 67 |
| Mean ± SD | 273 ± 66[5] | 13.5 ± 2.5[5] | 222 ± 129[5] | 1,047 ± 650[6] | 169 ± 65[5] | 186 ± 102[5] |

[1]Plasma was collected in EDTA and immediately kept at 4 degrees C. Free glucose was removed by chromatography on Sephadex G-25 and lipoproteins were isolated by sequential flotation. Fractions isolated included VLDL plus IDL (density (d) less than 1.019 grams/milliliter [g/ml]), LDL (d = 1.019-1.063 g/ml), and HDL (d = 1.063-1.21 g/ml). As judged by SDS-polyacrylamide gel electrophoresis, the LDL and HDL fractions contained less than 2 percent contaminating albumin, whereas the VLDL plus IDL fractions had less than 7 percent contamination. Plasma and isolated lipoproteins were incubated with 10 millimolar (mM) NaBH$_4$ for 4 hours at 37 degrees C., dialyzed against PBS and 0.025 ml (1-13 milligram/milliliter protein) added to the RIA. Antibody C6C9 was used at 1:4000, the glucitollysine standard at 10-0.05 nanomoles/milliliter and glc(RED)-LDL (48.7 percent of lysines glucosylated) for antigen coating at 5 micrograms/milliliter.
[2]For all seven normal LDL fractions assayed, no competition was observed at the level of protein added (1.70-3.28 mg/ml). Data given were calculated as the maximal number of glucitollysine residues that could have been detected. For statistical purposes, all normals were considered to have 47 picomoles glucitollysine/per milligram of protein.
[3]ND = not detectable; no binding was detected at the level of protein added.
[4]Not assayed.
[5]p (significant value) is less than 0.002, diabetic vs. normal.
[6]p is less than 0.02, diabetic vs. normal.

III. Plasma Assay for Glucosylated Proteins

To facilitate the identification of specific glucosylated proteins in large number of normal and diabetic subjects, a double antibody immunoassay was developed. This assay can be performed directly with plasma and does not require isolation of the proteins measured. Glucosylated apo B-containing lipoproteins and glucosylated albumin were measured. To assess the extent of glucosylation of apo B-containing lipoproteins in plasma, two human apo B-specific monoclonal antibodies, B14 and B18, were used (Curtiss et al. supra and Tsao et al., supra). The first antibody (B14) was used to bind and remove apo B-lipoproteins from plasma, and the second antibody (B18) was used to quantitate the amount of apo B-lipoproteins removed. Antibody B14 has identical affinity for apo B in VLDL, IDL and LDL. In preliminary studies it was demonstrated that antibodies B14 and B18 identified different epitopes on apo B and that glucosylation of LDL did not interfere with the binding of either antibody.

In this assay, NaBH$_4$-reduced plasmas were incubated with Sepharose-coupled apo B-specific antibody (B14) or Se-pharose-coupled albumin-specific antibody (AV45B6) at 4 degrees C. for 18 hours followed by removal of the plasma. An aliquot of the washed Sepharose B14 beads containing the apo B-lipoproteins was incubated at 4 degrees C. for 18 hours with immunochemically purified and radioiodinated apo B-specific antibody (B18) to verify that the same amount of apo B-lipoproteins were adsorbed from each plasma. A second aliquot of these beads was incubated with radioiodinated glucitollysine-specific antibody (G8H6) to quantitate the glucitollysine residues on the bound apo B-lipoproteins. After removal of the unbound radioiodinated antibody, the beads were counted and the antibody bound per tube quantitated.

Figure 7:
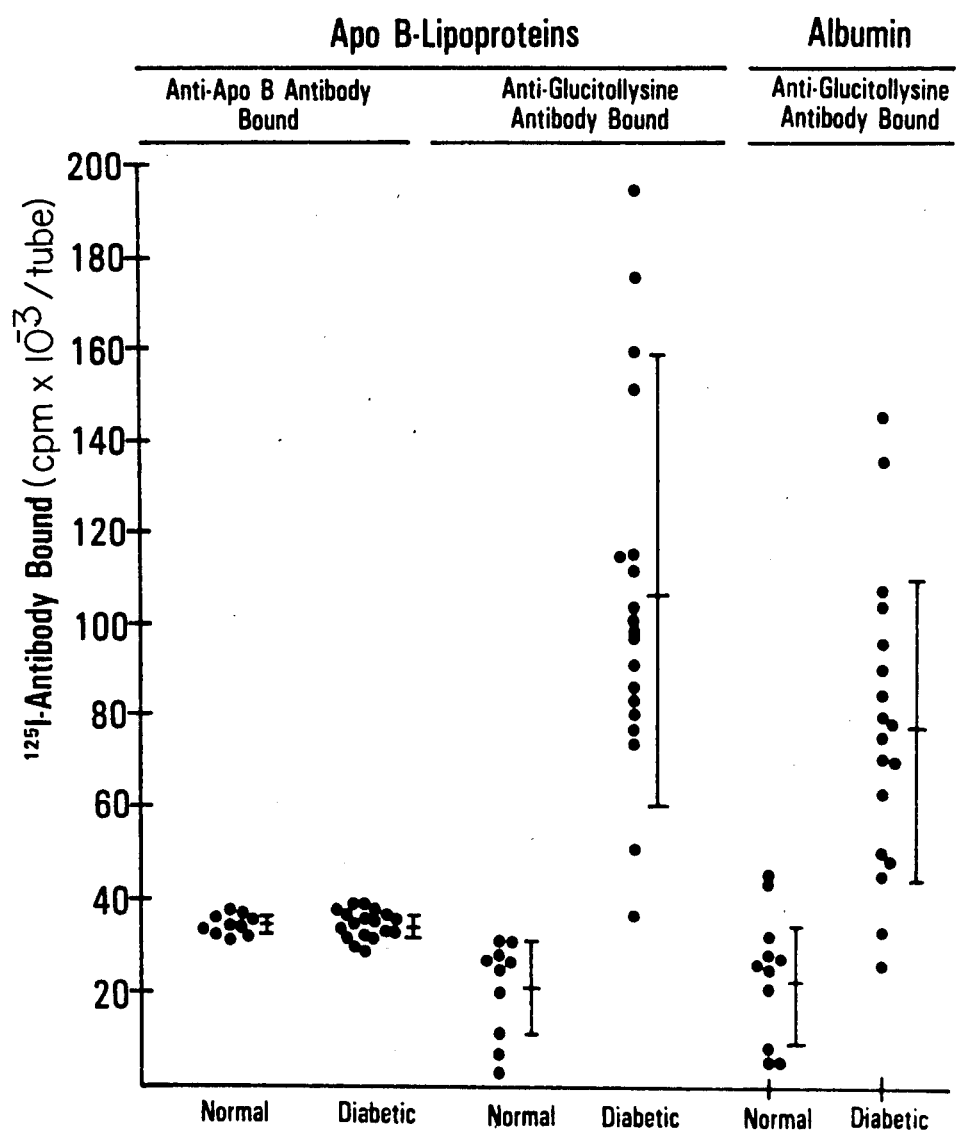
FIG. 7 illustrates the use of monoclonal antibodies of this invention to quantitate in plasma the extent of glucosylation of two plasma proteins [albumin and apoprotein B-lipoproteins (VLDL, IDL and LDL) in normoglycemic individuals and diabetic individuals. Immobilized apoprotein B (apo B-) or albumin specific first monoclonal antibodies were used to remove the apo B-lipoproteins or albumin from plasma by formation of binding complexes. After washing, glucitollysine residues on the albumin and LDL were quantitated by a second incubation with $^{125}$I-G6C9 antibody. Verification that equal amounts of apo B were removed from the normal and diabetic plasmas was obtained by quantitating the amount of apo B removed from plasma by incubation with a radioiodinated second non-cross-reacting apo B-specific antibody.

As shown in FIG. 7, the amount of $^{125}$I-B18 (apo B-specific) antibody bound per tube was similar for the 10 normal plasmas and the 18 diabetic plasmas tested. This verified that a given quantity of B14 antibody removed equal amounts of apo B-lipoprotein from normal and diabetic plasmas. In contrast, the mean amount of $^{125}$I-G8H6 (glucitollysine-specific) antibody bound was 5-fold higher in the diabetic plasmas compared with controls.

Similar assays employing an immobilized albumin-specific antibody (AV45B6) to remove albumin from plasma followed by quantitation of glucitollysine residues, identified similar differences in the degree of albumin glucosylation in the diabetic vs. normal plasmas. Including normal and diabetic patients (n=29), the correlation coefficient between nanogram quantities of glucitollysine antibody bound to the apo B-lipoproteins and the percent red blood cell HbA$_{lc}$ was r=0.848 (p less than 0.001).

Therefore, as previously demonstrated with isolated lipoprotein fractions, this assay identified and quantitated glucosylatd apo B-lipoproteins in plasma, and the degree of glucosylation was directly proportional to the clinical assessment of the degree of blood glucose control. With the proper availability and selection of protein-specific antibodies, this assay can be adapted to measure the extent of glucosylation of any protein of interest.

IV. Further Assays

In addition to the assays previously described herein, the receptors of this invention can also be utilized in still further assays.

In one assay the total amount of modification of the assayed protein is determined. Here, for example a known, predetermined amount of an epitope-specific reagent of this invention such as monoclonal antibody G8H6 that binds to free glucitollysine and glucitollysine modified protein is provided along with a known, predetermined amount of a hapten non-protein such as labeled glucitollysine. A known, predetermined amount of sample to be assayed is also provided. The three ingredients are admixed and the admixture is maintained for a period of time sufficient to form binding complexes between the monoclonal antibody and labeled glucitollysine and between the monoclonal antibody and glucitollysine-modified protein to be assayed. Trichloroacetic acid is then admixed in an amount sufficent to precipitate substantially all of the proteins present in the admixture. The amount of uncomplexed unprecipitated, labelled glucitollysine remaining in the supernatant is determined to thereby provide an assay of the amount of glucitollysine-modified protein that was present in the sample.

The label of the free glucitollysine can be a radioactive label such as $^{14}C$ in which case the precipitated proteins are preferably centrifuged to the bottom of the assay vessel and the supernatant containing unprecipitated, labeled glucitollysine is separated therefrom. The amount of radioactivity remaining in the supernatant is then determined to provide the assay as above.

The label of the free glucitollysine can also be a chromophoric label such as a dye that is bound to the glucitollysine molecule at a position away from the epitopic region of the molecule, such as at the carboxyl or alpha-amine groups. One such dye is N-(3-aminopropyl)-2,4-dinitroaniline which has an orange color at neutral pH values and shifts to a yellow color at acid pH values. Amide formation between the glucitollysine carboxyl group and the primary amine of the above chromophoric aniline provides the labeled glucitollysine.

Separation of precipitated proteins from the labeled, unprecipitated glucitollysine hapten is not required, although it may be utilized. Rather, the protein precipitate is permitted to settle, and the optical density of the supernatant provides a measure of the amount of uncomplexed, labeled glucitollysine present and thereby, indirectly the amount of modified, glucitollysine-containing protein that was present in the sample. This assay thus provides an example of a homogeneous assay.

V. Diagnostic Systems

A diagnostic system, preferably in kit form, comprises yet another embodiment of this invention. This system is useful for assaying for the presence of a hapten-modified protein in an assayed sample by the formation of an immune reaction. This system includes at least one package that contains biologically active epitope-specific reagent of this invention (hereinafter "receptor"). Thus, the receptor binds to a hapten-modified protein but not to an unmodified protein. When a predetermined amount of the receptor is admixed with a predetermined amount of an aqueous composition containing a hapten-modified protein, an immunological reaction occurs that forms a complex between the receptor and the modified protein.

Admixture between receptor and the modified protein occurs in an aqueous composition. However, either the receptor or the hapten-modified protein may be substantially dry and water-free prior to that admixture. Thus, a solution of the receptor in hybridoma supernatant, ascites fluid or buffer may be admixed with an aqueous cell extract to admix the reagents from two aqeuous compositions; the receptor may be coated on the walls of a microtiter plate and then admixed with a cell extract or serum containing the hapten-modified protein; or the hapten-modified protein may be coated on microtiter plate walls or on a nitrocellulose sheet or may be present in a tissue section and hybridoma supernatant, ascites fluid or a buffer solution containing the receptor admixed therewith.

Receptors are utilized along with an "indicating group" or a "label". The indicating group or label is utilized in conjunction with the receptor as a means for determining whether an immune reaction has taken place and an immunological complex has formed, and in some instances for determining the extent of such a reaction.

The indicating group may be a single atom as in the case of radioactive elements such as iodine 125 or 131, hydrogen 3, or sulfur 35, or carbon 14, or NMR-active elements such as fluorine 19 or nitrogen 15. The indicating group may also be a molecule such as a fluorescent dye like fluorescein, or an enzyme, such as horseradish peroxidase (HRP) or glucose oxidase, or the like.

The indicating group may be bonded to the receptor as where an antibody is labeled with $^{125}I$. The indicating group may also constitute all or a portion of a separate molecule or atom that reacts with the receptor molecule such as HRP-linked to rabbit anti-mouse antibodies where the antibody receptor was raised in a mouse, or where a radioactive element such as $^{125}I$ is bonded to protein A obtained from *Staphylococcus aureus*.

Where the principal indicating group is an enzyme such as HRP or glucose oxidase, additional reagents are required to visualize the fact that an immune reaction has occurred and the receptor-ligand complex has formed. Such additional reagents for HRP include hydrogen peroxide and an oxidation dye precursor such as diaminobenzidine. Additional reagents useful with glucose oxidase include ABTS dye, glucose and HRP.

The terms "indicating group" or "label" are used herein to include single atoms and molecules that are linked to the receptor or used separately, and whether those atoms or molecules are used alone or in conjunction with additional reagents. Such indicating groups or labels are themselves well-known in immunochemistry and constitute a part of this invention only insofar as they are utilized with otherwise novel receptors, methods and/or systems.

An indicating group or label is preferably supplied along with the receptor and may be packaged therewith or packaged separately. Additional reagents such as hydrogen peroxide and diaminobenzidine may also be included in the system when an indicating group such as HRP is utilized. Such materials are readily available in commerce, as are many indicating groups, and need not be supplied along with the diagnostic system. In addition, some reagents such as hydrogen peroxide decompose on standing, or are otherwise short-lived like some radioactive elements, and are better supplied by the end-user.

VI. Discussion

The epitope-specific reagent of the present invention comprises a receptor raised in an animal host to an immunogenic, hapten-modified protein. The immunogenic protein itself comprises a chemically modified protein, such as a hapten-modified low density lipoprotein, that is a homologous or autologous (self) protein as to the host animal and is non-immunogenic when introduced into the host as the unmodified homologous or autologous protein. The receptor binds to the hapten-modified, immunogenic protein but not to the unmodified protein.

Monoclonal antibodies that bind to reduced glycosylated human plasma lipoproteins but do not bind to non-reduced glycosylated or native non-reduced non-glycosylated human plasma lipoproteins are particularly preferred embodiments of the epitope-specific reagents. The conventional approach to form such antibodies would be to immunize mice with a human glycosylated protein with the hope that among the population of antigen specific antibody producing cells, some cells would be found that were specific for only the glycosylated protein. Such a selection, however, could only be accomplished after fusion and double screening of cloned hybridomas.

Previous experience in generating human LDL specific mouse monoclonal antibodies, for example, provided support for the proposition that human LDL is a potent immunogen in Balb/c mice [Curtiss et al. *J. Biol. Chem.* 257, 15213 (1982)], and thus the vast majority of hybridomas could be expected to be directed against epitopes of native LDL. This suggested that literally thousands of hybridomas might have to be double screened to identify the desired antibody.

If the immune response of the mouse was directed only against epitopes on LDL specific for the glucosylation modification, however, then a high percentage of the resulting hybridomas would produce the desired antibodies. To restrict the primary immune response, homologous mouse glc(RED)-LDL was used as both the primary and secondary immunogen, with the rationale that only the hapten-modified portions of homologous LDL would be immunogenic. To specifically propagate in vivo those clones of cells making antibodies against mouse glc(RED)-LDL that cross react with human glc(RED)-LDL, human glc(RED)-LDL was used as the final intravenous boster which was administered four days before fusion of the hybridoma. This short time interval was sufficient to allow proliferation of specific memory B cell clones, but was insufficient to allow primary stimulation and proliferation of clones recognizing epitopes on native human LDL.

Thus, from a single fusion, a large number of hybridomas was obtained which secreted antibody that was capable of binding human glc(RED)-LDL and 94 percent of these hybridomas did not produce antibody which bound normal human LDL. It should be emphasized that this technique produced a specific mouse antiserum as well.

The antibodies described herein were not specific only for glc(RED)-LDL, since they were also capable of binding to reduced glucosylated derivatives of other proteins including: HDL, human albumin, hemoglobin and transferrin. However, several lines of evidence suggest that each of these monoclonal antibodies is specific for a new epitope that resulted directly from the covalent attachment of glucose.

First, no reactions were observed with non-glucosylated human proteins including LDL, HDL, albumin, hemoglobin and transferrin. Second, LDL incubated with sodium cyanoborohydride in the absence of glucose did not inhibit the binding of any of the antibodies. Third, the degree of inhibition by glc(RED)-LDL for binding to each of the antibodies was directly related to the percent of lysine residues of LDL that contained glucose. Finally, the binding of each of the antibodies to glc(RED)-LDL could be completely inhibited by glucitollysine, the only detectable glucosylated amino acid residue of LDL [Witztum et al., *Diabetes,* 31, 382 (1982) and Schleicher et al., supra].

In spite of the fact that glucitollysine could completely inhibit the binding of each of the antibodies to glc(RED)-LDL, it is believed that the individual specificities of the antibody combining sites for antigen were not strictly identical. The degree of reactivity of each of these antibodies for the different human glc(RED)-proteins was not the same (See FIG. 5).

Therefore, the antigenicity of glucitollysine on each of the glucosylated and reduced proteins was influenced by the local environment. This local environment could have included both amino acids adjacent in the primary sequence to the conjugated glucitollysine together with distant amino acid residues that were spacially adjacent to the conjugated glucitollysine due to the folding of the secondary structure of the proteins.

Further evidence for heterogeneity in the antigen binding sites was obtained by comparing the ability of single amino acids and hexose sugars to inhibit binding. Whereas, it can not be absolutely determined that the ability of these compounds to inhibit antibody binding resulted only from their ability to occupy to some extent the antigen binding sites of the antibodies, the observation that the degree of inhibition with the different antibodies was heterogeneous with respect to both amino acids and sugars, suggests that this may be true.

With this assumption in mind, subtle differences in each of the antibody binding sites were identified. For example, sorbitol and mannitol, but not glucose or mannose, could completely inhibit the binding of antibody G6C9. Therefore, the open-chain hexose portion of glucitollysine plays a major role in the idiotope; i.e. the binding portion, of this antibody. This is the same antibody which had comparable reactivity for each of the glc(RED)-protein adducts (See FIG. 5) and suggested that the local environment may have less influence on the ability of this antibody to bind glucitollysine residues.

In contrast, the binding of antibodies G5E10, G8C11 and G5H3 was not inhibited by sorbitol or mannitol, but was inhibited by high concentrations of lysine or arginine. Therefore, the amino acid portion of glucitollysine may be more important in the antigen combining sites of these antibodies.

None of the monoclonal antibodies described herein bound glc(NR)-LDL (Table 1) or the glc(NR)-adducts of HDL, human albumin, hemoglobin or transferrin (data not shown) even though 6 percent of the lysine residues of each of these proteins contained covalently bound glucose. In contrast, glc(RED)-LDL that contained only 3.3 percent of the lysine residues glucosylated did compete (See FIG. 3). As predicted, non-reduced plasmas containing ketoamine and hemiketal Amadori rearrangement products also did not react with these antibodies (See FIG. 6). Since these non-reduced adducts exist in vivo in both normal individuals and in diabetic individuals (Table 4), it is possible that these adducts of glycosylation are "self determinants" and therefore are not immunogenic.

However, as demonstrated herein these plasma Amadori rearrangement products can be measured immunochemically in plasma after removal of free glucose by incubating plasma with sodium borohydride and reducing the ketoamine and hemiketal adducts to glucitollysine.

$HbA_{IC}$ measurements have been useful for both research applications and for the management of patients with diabetes mellitus [Bunn, *Diabetes,* 30, 613 (1981); Goldstein et al., *Diabetes,* 31 (Suppl. 3), 70 (1982); Bisse et al., *Diabetes,* 31, 630 (1982) and Yue et al., *Diabetes,* 31, 701 (1982)]. More recently, chromatographic and colorometric measurements of plasma proteins have demonstrated that non-enzymatically glucosylated plasma protein levels are approximately two to three times higher in diabetic individuals than in non-diabetic individuals; and such measurements suggest that the extent of glycosylation of total serum or plasma proteins is a good measure of short-term glycemia in diabetics [Kennedy et al., *Diabetes,* 31 (Suppl. 3), 52 (1982)].

The present invention demonstrates that glucosylated plasma proteins can also be identified and quantitated immunochemically. And, although only the plasmas of 35 subjects were examined (twelve normal, non-diabetic individuals and twenty-three diabetics). The five antibodies tested were capable of quantitating 2-10 fold higher level of glucitollysines residues in diabetic as compared to non-diabetic plasmas (Table 4 and 5).

Radioimmunoassay for glucosylated proteins with monoclonal antibodies offers a number of advantages including sensitivity and specificity. Furthermore, the present method provides the potential for distinguishing between Schiff base forms and the Amadori rearrangement products. For a single small volume of plasma, the total glucosylated protein can be readily measured after reduction of plasma with a non-specific reducing reagent, sodium borohydride, and the labile Schiff base form after reduction with sodium cyanoborohydride.

These antibodies are capable of identifying and quantitating glucitollysine residues in plasma. They are not, however, specific for glucosylated LDL or any other glucosylated protein when used as described herein. However, when these antibodies are used in conjunction with other protein-specific antibodies as described in the double antibody plasma assay, the techniques described herein can be employed to quantitate glucositollysine residues on any soluble or dispersible macromolecule including lipoproteins and other plasma proteins. In addition, they can be used to identify glucosylated membrane and cellular proteins by adapting the double antibody assay for use with microscopic examination of fixed cells or tissues.

The foregoing is intended as illustrative of the present invention but is not limiting. Numerous variations and modifications can be made without departing from the true spirit and scope of the novel concepts of the invention.

What is claimed is:

1. An epitope-specific reagent comprising a receptor raised in a host animal to an immunogenic, modified protein; said immunogenic, modified protein comprising a reduced glycosylated or alkylated free amine-modified plasma protein that when native and unmodified is (a) homologous or autologous to said host animal and (b) non-immunogenic in said host animal, said receptor binding to said reduced glycosylated or alkylated free amine-modified protein but not to said unmodified native protein.

2. The epitope-specific reagent according to claim 1 wherein said receptor is a monoclonal antibody.

3. The epitope-specific reagent according to claim 1 wherein said receptor is a monoclonal antibody produced and secreted by a hybridoma selected from the group consisting of hybridomas ATCC HB 8354, HB 8355, HB 8356, HB 8357, HB 8358 and HB 8359.

4. The epitope-specific reagent according to claim 1 wherein said receptor is in substantially pure form.

5. The epitope-specific reagent according to claim 1 wherein the immunogenic, modified protein is a reduced glycosylated plasma protein.

6. The epitope-specific reagent according to claim 1 wherein the native unmodified protein is a plasma protein selected from the group consisting of a lipoprotein, hemoglobin, albumin and transferrin.

7. A method of formig an epitope-specific receptor comprising the steps of:

(a) administering to a host an immunogenic, reduced glycosylated or alkylated free amine-modified plasma protein in an amount sufficient to induce the production of antibodies to the epitope of the reduced glycosylated or alkylated free amine-modified plasma protein, the native plasma protein being non-immunogenic in the host in an unmodified native form; and (b) recovering the antibodies so produced.

8. The method according to claim 7 wherein the immunogenic, reduced glycosylated or alkylated free amine-modified plasma protein is a reduced glycosylated plasma protein.

9. The method according to claim 7 wherein the protein in unmodified form is a native plasma protein selected from the group consisting of a lipoprotein, hemoglobin, albumin and transferrin.

10. A method of forming a monoclonal anitbody for use as an epitope-specific reagent comprising the steps of:

(a) administering to a host an immunogenic, reduced glycosylated or alkylated free amine-modified plasma protein in an amount sufficient to induce the production of antibodies to the epitope of the reduced glycosylated or alkylated free amine-modified plasma protein, the protein being non-immunogenic in the host in an unmodified native form;

(b) recovering antibody producing cells from the host;

(c) forming cell hybridomas by fusing the antibody producing cells with myeloma cells;

(d) culturing the hybridomas so formed; and (e) collecting the monoclonal antibodies as a product of said hybridomas.

11. The method according to claim 10 wherein said receptor is in substantially pure form.

12. The method according to claim 10 further including the step of administering to said host, after step (a) but before step (b), a second immunogenic plasma protein in a reduced glycosylated or alkylated free amine-modified form in an amount sufficient to enhance the proliferative expansion and differentiation of B cell clones producing antibodies capable of crossreacting with the epitope of said first-named reduced glycosylated or alkylated free amine-modified protein, the second protein being immunogenic in the host in an unmodified native form.

13. The method according to claim 10 wherein the epitope-specific reagent is a monoclonal antibody produced and secreted by a hybridoma selected from the group consisting of hybridomas ATCC HB 8355, HB 8356, HB 8357, HB 8359, HB 8358 and HB 8354.

14. The method according to claim 10 wherein the reduced glycosylated or alkylated free amine-modified form of the immunogenic protein is a reduced glycosylated plasma protein.

15. The method according to claim 10 wherein the protein in unmodified form is a native plasma protein selected from the group consisting of a lipoprotein, hemoglobin, albumin and transferrin.

16. A monoclonal antibody which immunoreacts with a reduced glycosylated free amine-modified plasma protein but does not immunoreact with the non-reduced non-glycosylated native protein prepared by the method comprising the steps of:

(a) administering to a host a reduced glucosylated free amine-modified plasma protein in an amount sufficient to induce the production of antibodies to the reduced glycosylated free amine-modified plasma protein, said non-reduced non-glycosylated native protein being non-immunogenic in the host;
(b) recovering the antibody producing cells from the host;
(c) forming cell hybrids by fusing said antibody producing cells to myeloma cells;
(d) culturing said hybrids; and
(e) collecting said monoclonal antibody as a product of said hybrids.

17. A method of preparing a monoclonal antibody which immunoreacts with a reduced glucosylated free amine-modified plasma protein but does not immunoreact with the non-reduced non-glucosylated native protein comprising the steps of (a) culturing the hybridoma ATCC HB 8355 in the suitable medium and (b) recovering the antibody from the supernatant above the hybridoma.

18. The method according to claim 17 wherein said non-reduced non-glucosylated native protein is a plasma protein selected from the group consisting of a lipoprotein, hemoglobin, albumin and transferrin.

19. The monoclonal antibody prepared by the method of claim 17.

20. A method of preparing a monoclonal antibody which immunoreacts with a reduced glucosylated free amine-modified plasma protein but does not immunoreact with the non-reduced non-glucosylated native protein comprising the steps of (a) culturing the hybridoma ATCC HB 8356 in a suitable medium and (b) recovering the antibody from the supernatant above the hybridoma.

21. The method according to claim 20 wherein said non-reduced non-glucosylated protein native is a plasma protein selected from the group consisting of a lipoprotein, hemoglobin, albumin and transferrin.

22. The monoclonal antibody prepared by the method of claim 20.

23. A method of preparing a monoclonal antibody which immunoreacts with a reduced glucosylated free amine-modified plasma protein but does not immunoreact with the non-reduced non-glucosylated native protein comprising the steps of (a) culturing the hybridoma ATCC HB 8357 in a suitable medium and (b) recovering the antibody from the suernatant above the hybridoma.

24. The method according to claim 23 wherein said non-reduced non-glucosylated protein native is a plasma protein selected from the group consisting of a lipoprotein, hemoglobin, albumin and transferrin.

25. The monoclonal antibody prepared by the method of claim 23.

26. A method of preparing a monoclonal antibody which immunoreacts with a reduced glucosylated free amine-modified plasma protein but does not immunoreact with the non-reduced non-glucosylated native protein comprising the steps of (a) culturing the hybridoma ATCC HB 8359 in a suitable medium and (b) recovering the antibody from the supernatant above the hybridoma.

27. The method according to claim 26 wherein said non-reduced non-glycosylated native protein is a plasma protein selected from the group consisting of a lipoprotein, hemoglobin, albumin and transferrin.

28. The monoclonal antibody prepared by the method of claim 26.

29. A method of preparing a monoclonal antibody which immunoreacts with a reduced glucosylated free amine-modified plasma protein but does not immunoreact with the non-reduced non-glucosylated native protein comprising the steps of (a) culturing the hybridoma ATCC HB 8358 in a suitable medium and (b) recovering the antibody from the supernatant above the hybridoma.

30. The method according to claim 29 whrein said non-reduced non-glucosylated native protein is a plasma protein selected from the group consisting of a lipoprotein, hemoglobin, albumin and transferrin.

31. The monoclonal antibody prepared by the method of claim 29.

32. A method of preparing a monoclonal antibody which immunoreacts with a reduced glucosylated free amine-modified plasma protein but does not immunoreact with the non-reduced non-glucosylated native protein comprising the steps of (a) culturing the hybridoma ATCC HB 8354 in a suitable medium and (b) recovering the antibody from the supernatant above the hybridoma.

33. The method according to claim 32 wherein said non-reduced non-glucosylated native protein is a plasma protein selected from the group consisting of a lipoprotein, hemoglobin, albumin and transferrin.

34. The monoclonal antibody prepared by the method of claim 32.

35. A method of preparing a monoclonal antibody which immunoreacts with a reduced glucosylated free amine-modified plasma protein but does not immunoreact with the non-reduced non-glucosylated native protein comprising the steps of injecting the hybridoma ATCC HB 8355 into a host and recovering the antibody from the ascites fluid.

36. The method according to claim 35 wherein said non-reduced non-glucosylated native protein plasma protein selected from the group consisting of a lipoprotein, hemoglobin, albumin and transferrin.

37. The monoclonal antibody prepared by the method of claim 35.

38. A method of preparing a monoclonal antibody which immunoreacts with a reduced glucosylated free amine-modified plasma protein but does not immunoreact with the non-reduced non-glucosylated native protein comprising the steps of injecting the hybridoma ATCC HB 8356 into a host and recovering the antibody from the ascites fluid.

39. The method according to claim 38 wherein said non-reduced non-glucosylated native protein is a plasma protein selected from the group consisting of a lipoprotein, hemoglobin, albumin and transferrin.

40. The monoclonal antibody prepared by the method of claim 38.

41. A method of preparing a monoclonal antibody which immunoreacts with a reduced glucosylated free amine-modified plasma protein but does not immunoreact with the non-reduced non-glucosylated native protein comprising the steps of injecting the hybridoma ATCC HB 8357 into a host and recovering the antibody from the ascites fluid.

42. The method according to claim 41 wherein said non-reduced non-glucosylated native protein is a plasma protein selected from the group consisting of a lipoprotein, hemoglobin, albumin and transferrin.

43. The monoclonal antibody prepared by the method of claim 41.

44. A method of preparing a monoclonal antibody which immunoreacts with a reduced glucosylated free amine-modified plasma protein but does not immunoreact with the non-reduced non-glucosylated native protein comprising the steps of injeting the hybridoma ATCC HB 8359 into a host and recovering the antibody from the ascites fluid.

45. The method according to claim 44 wherein said non-reduced non-glucosylated native protein is a plasma protein selected from the group consisting of a lipoprotein, hemoglobin, albumin and transferrin.

46. The monoclonal antibody prepared by the method of claim 44.

47. A method of preparing a monoclonal antibody which immunoreacts with a reduced glucosylated free amine-modified plasma protein but does not immunoreact with the non-reduced non-glucosylated native protein comprising the steps of injecting the hybridoma ATCC HB 8358 into a host and recovering the antibody from the ascites fluid.

48. The method according to claim 47 wherein said non-reduced non-glucosylated native protein is a plasma protein selected from the group consisting of a lipoprotein, hemoglobin, albumin and transferrin.

49. The monoclonal antibody prepared by the method of claim 47.

50. A method of preparing a monoclonal antibody which immunoreacts with a reduced glucosylated free amine-modified plasma protein but does not immunoreact with the non-reduced non-glucosylated native protein comprising the steps of injecting the hybridoma ATCC HB 8354 into a host and recovering the antibody from the ascites fluid.

51. The method according to claim 50 wherein said non-reduced non-glucosylated native protein is a plasma protein selected from the group consisting of a lipoprotein, hemoglobin, albumin and transferrin.

52. The monoclonal antibody prepared by the method of claim 50.

53. A diagnostic system for assaying for the presence of an antigenic reduced glycosylated or alkylated free amine-modified protein, said system in kit form including in at least one package as an active ingredient an effective amount of an epitope-specific reagent which when introduced into a sample reacts with an antigenic, reduced glycosylated or alkylated free amine-modified protein but does not react with an unmodified native protein as a measure of the reduced glycosylated or alkylated free amine-modified protein in the sample.

54. The diagnostic system according to claim 53 further including a second package including a label for identifying the presence of said unmodified protein.

55. The diagnostic system according to claim 53 wherein the epitope-specific reagent is a monoclonal antibody.

56. The diagnostic system according to claim 53 wherein said reduced glycosylated or alkylated free amine-modified protein is a reduced glycosylated plasma protein.

57. A method for assaying for the presence of an antigenic, reduced glycosylated or alkylated free amine-modified protein in a sample comprising:
   (a) providing an epitope-specific reagent comprising a receptor raised in a host animal to an immunogenic, modified protein, said immunogenic, modified protein comprising a reduced glycosylated or alkylated free amine-modified plasma protein that when in unmodified native form is (i) homologous or autologous to said host animal and (ii) non-immunogenic in said host animal, said receptor binding to said reduced glycosylated or alkylated free amine-modified plasma protein but not to said unmodified native protein;
   (b) admixing a predetermined amount of the epitope-specific reagent with a predetermined amount of sample to be assayed for the presence of the antigenic, reduced glycosylated or alkylated free amine-modified protein to which the epitope-specific reagent binds;
   (c) maintaining that admixture for a period of time sufficient for said epitope-specific reagent to bind to the antigenic, reduced glycosylated or alkylated free amine-modified protein present in the admixed sample; and
   (d) determining the amount of binding between said epitope-specific reagent and said antigenic, reduced glycosylated or alkylated free amine-modified protein.

58. An assay for determining the presence and amount of an antigenic, reduced glycosylated or alkylated free amine-modified protein comprising the steps of:
   (a) providing a first receptor covalently attached in a known amount to a solid support, the first receptor binding to a first epitope of a protein to be assayed when the protein is in reduced glycosylated or alkylated free amine-modified and unmodified native forms;
   (b) providing a second receptor that binds to a second epitope of the protein to be assayed when that protein is in reduced glycosylated or alkylated free amine-modified or unmodified native forms;
   (c) providing an epitope-specific reagent comprising a receptor raised in a host animal to an immunogenic, modified protein, said immunogenic, modified protein comprising a reduced glycosylated or alkylated free amine-modified plasma protein that when in unmodified native form is (i) homologous or autologous to said host animal and (ii) non-immunogenic in said host animal, said receptor binding to said reduced glycosylated or alkylated free amine-modified plasma protein but not to said unmodified native protein, said epitope-specific reagent binding to a third epitope of the protein that is present only when the protein is in reduced glycosylated or alkylated free amine-modified form;
   (d) admixing a predetermined amount of said covalently attached first receptor and a predetermined amount of a sample to be assayed (i) for the presence of antigenic, reduced glycosylated or alkylated free amine-modified protein to which the epitope-specific reagent binds, and (ii) for the presence of the unmodified native protein to which the first and the second receptors bind;
   (e) maintaining that admixture for a period of time sufficient for said covalently attached first receptor to bind reduced glycosylated or alkylated free amine-modified and unmodified native proteins present and form binding complexes therewith;
   (f) separating the formed binding complexes from the remainder of the admixture;
   (g) dividing the formed binding complexes into at least a first aliquot and a second aliquot;
   (h) admixing the first aliquot with a predetermined amount of the second receptor and maintaining that admixture for a period of time sufficient to form second binding complexes between the second receptor and the first-formed binding complexes;

(i) determining the amount of second binding complexes formed to thereby determine the total amount of both reduced glycosylated or alkylated free amine-modified and unmodified protein present in the sample;

(j) admixing the second aliquot with a predetermined amount of the epitope-specific reagent and maintaining that admixture for a period of time sufficient to form a third binding complex between the eiptope-specific reagent and reduced glycosylated or alkylated free amine-modified protein present in the first-formed binding complexes; and (k) determining the amount of third binding complex formed to thereby determine the amount of reduced glycosylated or alkylated free amine-modified protein present in the sample.

59. A monoclonal antibody produced and secreted by a hybridoma formed by fusion of a cell from a mouse myeloma cell line and a spleen cell from a mouse previously immunized first with a murine reduced glucosylated free amine-modified plasma protein and then boosted with a human reduced glucosylated free amine-modified plasma protein to enhance the proliferative expansion and differentiation of B cell clones producing antibodies capable of crossreacting with said murine reduced free amine-glucosylted plasma protein, said antibody reacting with the human reduced glucosylated free amine-modified plasma protein, glucitollysine, glucitolpolylysine, arginine and lysine, but not with a non-reduced glucosylated free amine-modified plasma protein, a reduced non-glucosylated plasma protein, a non-reduced non-glucosylated native protein, methionine, sorbitol, manitol, glutamine or glucose.

60. The monoclonal antibody according to claim 59 which is of the class IgG.

61. The monoclonal antibody according to claim 59 which is produced and secreted by a hybridoma formed by fusion of P3×63Ag8 myeloma cells and spleen cells from a Balb/c mouse.

62. The monoclonal antibody according to claim 59 wherein said murine reduced glucosylated free amine-modified plasma protein and said human rediced glucosylated free amine-modified plasma protein when in non-reduced and non-glucosylated native forms are selected from the group consisting of a lipoprotein, hemoglobin, albumin and transferrin.

63. A monoclonal antibody produced and secreted by a hybridoma formed by fusion of a cell from a mouse myeloma cell line and a spleen cell from a mouse previously immunized first with a murine reduced glucosylated free amine-modified plasma protein and then boosted with a human reduced glucosylated free amine-modified plasma protein to enhance the proliferative expansion and differentiation of B cell clones producing antibodies capable of crossreacting with said murine reduced glucosylated free amine-plasma protein, said antibody reacting with the human reduced glucosylated free-amine-modified plasma protein, glucitollysine, glucitolpolylysine, arginine, lysine, methionine, sorbitol and mannitol, but not with a non-reduced glucosylated free amine-modified plasma protein, a reduced non-glucosylated plasma protein, a non-reduced non-glucosylated native plasma protein, glutamine or glucose.

64. The monoclonal antibody according to claim 63 which is of the class IgG.

65. The monoclonal antibody according to claim 63 which is produced and secreted by a hybridoma formed by fusion of P3×63Ag8 myeloma cells and spleen cells fron a Balb/c mouse.

66. The monoclonal antibody according to claim 63 wherein said murine reduced glucosylated free amine-modified plasma protein and said human reduced glucosylated free amine-modified plasma protein when in non-reduced and non-glucosylated native forms are selected from the group consisting of a lipoprotein, hemoglobin, albumin and transferrin.

67. A monoclonal antibody produced and secreted by a hybridoma formed by fusion of a cell from a mouse myeloma cell line and a spleen cell from a mouse previously immunized first with a murine reduced glucosylated free amine-modified plasma protein and then boosted with a human reduced glucosylated free amine-modified plasma protein to enhance the proliferative expansion and differentiation of B cell clones producing antibodies capable of crossreacting with said murine reduced glucosylated free amine-modified plasma protein, said antibody reacting with the human reduced glucosylated free amine-modified plasma protein, glucitollysine, glucitolpolylysine and arginine, but not with a non-reduced glucosylated free amine-modified plasma protein, a reduced non-glucosylated plasma protein, a non-reduced non-glucosylated native plasma protein, lysine, methionine, sorbitol, mannitol, glutamine or glucose.

68. The monoclonal antibody according to claim 67 which is of the class IgG.

69. The monoclonal antibody according to claim 67 which is produced and secreted by a hybridoma formed by fusion of P3×63Ag8 myeloma cells and spleen cells from a Balb/c mouse.

70. The monoclonal antibody according to claim 67 wherein said murine reduced glucosylated free amine-modified plasma protein and said human reduced glucosylated free amine-modified plasma protein when in non-reduced and non-glucosylated native forms are selected from the group consisting of a lipoprotein, hemoglobin, albumin and transferrin.

71. A monoclonal antibody produced and secreted by a hybridoma formed by fusion of a cell from a mouse myeloma cell line and a spleen cell from a mouse previously immunized first with a murine reduced glucosylated free amine-modified plasma protein and then boosted with a human reduced glucosylated free amine-modified plasma protein to enhance the proliferative expansion and differentiation of B cell clones producing antibodies capable of crossreacting with said murine reduced glucosylated free amine-modified plasma protein, said antibody reacting with the human reduced glucosylated free amine-modified plasma protein, glucitollysine, glucitolpolylysine, lysine, methionine, sorbitol and glutamine, but not with a non-reduced glucosylated free amine-modified plasma protein, a reduced non-glycosylated protein, a non-reduced non-glucosylated native plasma protein, arginine, mannitol or glucose.

72. The monoclonal antibody according to claim 71 which is of the class IgG.

73. The monoclonal antibody according to claim 71 which is produced and secreted a hybridoma formed by fusion of P3×63Ag8 myeloma cells and spleed cells fropm a Balb/c mouse.

74. The monoclonal antibody according to claim 71 wherein said murine reduced glucosylated free amine-modified plasma protein and said human reduced glucosylated free amine-modified plasma protein when in non-reduced and non-glucosylated native forms are selected from the group consisting of a lipoprotein, hemoglobin, albumin and tranferrin.

75. A monoclonal antibody produced and secreted by a hybridoma formed by fusion of a cell from a mouse myeloma cell line and a spleen cell from a mouse previously immunized first with a murine reduced glucosylated free amine-modified plasma protein and then boosted with a human reduced glucosylated free amine-modified plasma protein to enhance the proliferative expansion and differentiation of B cell clones producing antibodies capable of crossreacting with said murine reduced glucosylated free amine-modified plasma protein, said antibody reacting with the human reduced glucosylated free amine-modified plasma protein glucitollysine, glucitolpolylysine and sorbitol, but not with a non-reduced glucosylated free amine-modified plasma protein, a reduced non-glucosylated plasma protein, a non-reduced non-glucosylated native plasma protein, arginine, lysine, methionine, mannitol, glutamine or glucose.

76. The monoclonal antibody according to claim 75 which is of the class IgM.

77. The monoclonal antibody according to claim 75 which is produced and secreted by a hybridoma formed by fusion of P3×63Ag8 myeloma cells and spleen cells from a Balb/c mouse.

78. The monoclonal antibody according to claim 75 wherein said murine reduced glucosylated free amine-modified plasma protein and said human reduced glucosylated free amine-modified plasma protein when in non-reduced and non-glucosylated native forms are selected from the group consisting of a lipoprotein, hemoglobin, albumin and transferrin.

79. A hybridoma having ATCC accession number HB 8355.

80. The monoclonal receptor that reacts with glucilollysine and is produced and secreted by the hybridoma of claim 79.

81. A hybridoma having ATCC accession number HB 8356.

82. The monoclonal receptor tht reacts with glucitollysine and is produced and secreted by the hybridoma of claim 81.

83. A hybridoma having ATCC accession number HB 8357.

84. The monoclonal receptor that reacts with glucitollysine and is produced and secreted by the hybridoma of claim 83.

85. A hybridoma having ATCC accession number HB 8358.

86. The monoclonal receptor that reacts with glucitollysine and is produced and secreted by the hybridoma of claim 85.

87. A hybridoma having ATCC accession number HB 8359.

88. The monoclonal receptor that reacts with glucitollysine and is produced and secreted by the hybridoma of claim 87.

89. A hybridoma having ATCC accession number HB 8354.

90. The monoclonal receptor that reacts with glucitollysine and is produced and secreted by the hybridoma of claim 89.

* * * * *

UNITED STATES PATENT AND TRADEMARK OFFICE
CERTIFICATE OF CORRECTION

PATENT NO. : 4,778,752
DATED : October 18, 1988
INVENTOR(S) : Curtiss et al.

It is certified that error appears in the above-identified patent and that said Letters Patent is hereby corrected as shown below:

Column 1, after the title and before the first paragraph, insert the following paragraph:

--This invention was made with government support under Contract No. HL 14197 awarded by the National Institutes of Health. The government has certain rights in the invention.--

Signed and Sealed this

Fourth Day of January, 1994

*Attest:*

BRUCE LEHMAN

*Attesting Officer*     *Commissioner of Patents and Trademarks*